US012472302B2

(12) United States Patent
Radl et al.

(10) Patent No.: US 12,472,302 B2
(45) Date of Patent: Nov. 18, 2025

(54) EXTERNAL FEMALE CATHETER SYSTEM AND METHOD OF USE

(71) Applicant: Boehringer Technologies, LP, Phoenixville, PA (US)

(72) Inventors: Christopher L. Radl, Malvern, PA (US); Michael Reed Vennel, Phoenixville, PA (US); William Charles Dackis, Philadelphia, PA (US)

(73) Assignee: Shortridge Holdings, LLC, Phoenixville, PA (US)

( * ) Notice: Subject to any disclaimer, the term of this patent is extended or adjusted under 35 U.S.C. 154(b) by 460 days.

(21) Appl. No.: 18/074,714

(22) Filed: Dec. 5, 2022

(65) Prior Publication Data

US 2023/0099821 A1 Mar. 30, 2023

Related U.S. Application Data

(60) Continuation-in-part of application No. 17/750,720, filed on May 23, 2022, now Pat. No. 12,220,520, and
(Continued)

(51) Int. Cl.
*A61M 1/00* (2006.01)
*A61F 5/455* (2006.01)
*A61M 25/00* (2006.01)

(52) U.S. Cl.
CPC ............. *A61M 1/743* (2021.05); *A61F 5/455* (2013.01); *A61M 1/742* (2021.05); *A61M 2025/0056* (2013.01); *A61M 2202/0496* (2013.01)

(58) Field of Classification Search
CPC .......... A61M 27/00; A61M 1/74; A61M 1/75; A61M 1/84; A61M 2202/0496;
(Continued)

(56) References Cited

U.S. PATENT DOCUMENTS 4,023,560 A * 5/1977 Cade ........................ A61F 5/455
600/574
4,465,481 A 8/1984 Blake
(Continued)

FOREIGN PATENT DOCUMENTS

WO 2014085099 A1 6/2014

OTHER PUBLICATIONS

Wire, 2025, Cambridge Dictionary. (Year: 2025).*
(Continued)

*Primary Examiner* — Philip R Wiest
*Assistant Examiner* — Brandon W. Levy
(74) *Attorney, Agent, or Firm* — Caesar Rivise, PC

(57) ABSTRACT

System and methods for automatically removing by suction urine voided by a female. The systems include an external catheter and an integrated suction regulator or a stand alone external catheter for use with any source of regulated suction. The external catheter includes a suction tube an a fluid pervious cover. The catheter's cover is applied at the female's urethra opening to receive urine voided by the female, whereupon urine from the external female catheter passes through the cover into the suction tube, from which it is carried by out of the external catheter for collection. The external catheter is malleable so that it can be conformed to the anatomy of the female.

8 Claims, 12 Drawing Sheets

Related U.S. Application Data a continuation-in-part of application No. 17/179,998, filed on Feb. 19, 2021, now Pat. No. 11,547,788, said application No. 17/750,720 is a continuation-in-part of application No. 16/996,214, filed on Aug. 18, 2020, now Pat. No. 11,395,871, said application No. 17/179,998 is a division of application No. 16/996, 214, filed on Aug. 18, 2020, now Pat. No. 11,395,871.

(60) Provisional application No. 62/924,326, filed on Oct. 22, 2019.

(58) Field of Classification Search
CPC .......... A61M 2210/1085; A61M 25/04; A61M 1/0023; A61M 1/743; A61M 1/742; A61M 1/90; A61M 25/0017; A61M 25/007; A61M 1/964; A61M 25/0021; A61M 25/09; A61M 3/0279; A61M 1/7415; A61M 2025/0056; A61M 2025/0057; A61M 2205/0205; A61F 5/455; A61F 5/453; A61F 13/0203; A61F 2002/047; A61B 10/007; A61B 2017/306; A61B 2217/005
See application file for complete search history.

(56) References Cited

U.S. PATENT DOCUMENTS 4,610,675 A 9/1986 Triunfol
4,747,166 A * 5/1988 Kuntz .................... A61F 5/455 4/144.1
4,815,151 A * 3/1989 Ball ...................... A61F 5/4556 4/144.1
4,840,625 A * 6/1989 Bell ....................... A61F 5/453 604/352
4,932,948 A * 6/1990 Kernes ................... A61F 5/453 128/885
5,073,172 A 12/1991 Fell
5,678,564 A * 10/1997 Lawrence ............... A61F 5/455 600/573
5,713,880 A * 2/1998 Anderson ............... A61F 5/453 604/352
5,894,608 A 4/1999 Birbara
6,024,120 A 2/2000 Yam et al.
6,849,065 B2 2/2005 Schmidt et al.
7,018,366 B2 3/2006 Easter
7,220,250 B2 5/2007 Suzuki et al.
8,287,508 B1 10/2012 Sanchez
9,101,515 B2 * 8/2015 Odermatt .............. A61M 1/916
10,099,027 B2 * 10/2018 Cole ................. A61M 16/0475
10,646,625 B2 5/2020 Radl et al.
2003/0004496 A1 * 1/2003 Tanghoj ............ A61M 25/0017 604/544
2004/0006311 A1 1/2004 Shchervinsky
2004/0006331 A1 * 1/2004 Shchervinsky ....... A61M 27/00 604/541
2005/0192548 A1 9/2005 Dolliver et al.
2005/0197639 A1 9/2005 Mombrinie
2007/0010798 A1 1/2007 Stoller et al.
2008/0287894 A1 * 11/2008 Van Den Heuvel .... A61F 5/455 604/327
2010/0094173 A1 * 4/2010 Denton ............... A61M 1/7415 604/323
2012/0238972 A1 9/2012 Karpowicz et al.
2013/0053793 A1 2/2013 Locke
2016/0310711 A1 10/2016 Luxon et al.
2017/0266031 A1 * 9/2017 Sanchez .................. A61F 5/443

OTHER PUBLICATIONS

Https://www.crbard.com/Medical/en-US/Products/PUREWICK-Female-External-Catheter, undated, 1 page.
Https://www.ohmedical.com/External-Catheters/DRYDOCtrade-VACUUM-STATION—DD15/, 2020, 2 pages.
Https://sageproducts.com/primafit-external-urine-management-system-for-females/, 2020, 3 pages.

* cited by examiner 10
12
12A
12B
14
16
18
20
22
24
24A
26
36
38

22
22B
22C
22E
22F
24
38
48
56
58
80
82
84

48
5
46
38
64
42
26
34
30
32
28
52
66
48A
24A
40
24B
22G
22B
22A
22C
22F
22E 44
54
46
64
26
34
48B
30
32
68
52
28
80
66
92
42
40
48A
48

86
40
30
32
48A
48B
50
46
86
34

10
12
12A
12B
14
16
18
24
24A
24B'
26
36
38
120
122
122A
122B
124
126
128
84
24'
52
60
56
124A
124B
128B
130
132A
132D
134A
134D
136

EXTERNAL FEMALE CATHETER SYSTEM AND METHOD OF USE

CROSS-REFERENCE TO RELATED APPLICATIONS

The current application is a Continuation-In-Part and claims the benefit of 35 U.S.C. § 120 of U.S. patent application Ser. No. 17/179,998, filed on Feb. 19, 2021, entitled "Method of Use of External Female Catheter System with Integrated Suction Regulator, which in turn claims priority under 35 U.S.C. § 121 of utility application Ser. No. 16/996,214, filed on Aug. 18, 2020, entitled "External Female Catheter System With Integrated Suction Regulator and Method of Use", now U.S. Pat. No. 11,395,871, which in turn claims the benefit under 35 U.S.C. § 119(e) of Provisional Application Ser. No. 62/924,326, filed on Oct. 22, 2019, entitled "External Female Catheter System With Integrated Suction Regulator and Method of Use". This current application is also a Continuation-in-Part application and claims the benefit under 35 U.S.C. § 120 of Ser. No. 17/750,720, filed on May 23, 2022 entitled "Leakage Resistant External Female Catheter System and Method of Use" which in turn is a Continuation-in-Part and claims the benefit of 35 U.S.C § 120 of Ser. No. 16/996,214, filed on Aug. 18, 2020, entitled "External Female Catheter System With Integrated Suction Regulator and Method of Use", now U.S. Pat. No. 11,395,871, which claims the benefit under 35 U.S.C. § 119 (e) of Provisional Application Ser. No. 62/924,326, filed on Oct. 22, 2019. The entire disclosures of all of the aforementioned patent applications are incorporated by reference herein for all purposes.

SPECIFICATION

Field of the Invention

This invention relates generally to medical devices and methods and more particularly to devices and methods for automatically removing urine from a female patient using suction applied to an external catheter.

Background of the Invention

Various external catheters are available for non-invasive urine output management in female patients. The PUREWICK® female external catheter available from C.R. Bard, Inc. is an example of one such device. That external catheter is a soft member having a hollow flexible body including a side opening exposing soft absorbent gauze. The catheter is configured to be positioned so that soft gauze is disposed between the patient's separated gluteus and labia and in fluid communication with the urethral opening of the patient, whereupon urine voided by the patient is wicked into the gauze. The catheter is arranged to be attached via suction tubing to a suction canister, which should in turn be connected to either a suction regulator on a hospital wall or a portable suction pump, such as the DRYDOC™ vacuum suction station of C.R. Bard, Inc., whereupon the urine wicked into the external catheter is carried by the suction into the canister for collection. The Instructions for Use (IFU) of the PUREWICK® female external catheter indicates that the suction source should be set to a minimum of 40 mmHG continuous suction.

Sage Products, LLC, now a Stryker Corporation company, provides an external urine management system for females under the trademark PRIMAFIT. That system is in many respects similar to the PUREWICK® system. In particular, the PRIMAFIT system basically comprises an external catheter body having an end cap to fit in the woman's perineal area to secure the catheter in place. The catheter includes soft wicking fabric that absorbs and diverts urine away from the patient's skin. Urine is then absorbed into the system's core and suctioned into a collection canister.

The patent literature includes various systems and methods for collecting and transporting urine away from a person's body, such as: U.S. Pat. No. 4,610,675 (Triunfol); U.S. Pat. No. 4,747,166 (Kuntz); U.S. Pat. No. 5,678,564 (Lawrence et al.); U.S. Pat. No. 5,894,608 (Birbara); U.S. Pat. No. 6,849,065 (Schmidt et al.); U.S. Pat. No. 7,018,366 (Easter); U.S. Pat. No. 7,220,250 (Suzuki et al.); and U.S. Pat. No. 8,287,508 (Sanchez).

As will be appreciated by those skilled in the art, most hospital suction regulators provide insufficient flow at low vacuum pressures, like the 40 mmHg recommended for use with the PUREWICK® female external catheter. Therefore nurses or other care givers frequently increase the vacuum to get adequate urine flow. However, the use of higher vacuum pressure poses an increased risk to the patient, as the only opening in the circuit for air to relieve the pressure is adjacent the patient's genitalia. Accordingly, use of increased vacuum pressure to increase the flow rate of urine being withdrawn into the canister runs the risk of injury to the delicate issue adjacent the urethral opening. In our U.S. Provisional Patent Application Ser. No. 62/829,731, filed on Apr. 5, 2019, entitled System Including Suction Regulator For Automatically Removing Urine From A Female Patient And Method Of Use Of The System, which is assigned to the same assignee as this invention, there is disclosed and claimed a disposable suction regulator configured for use between the female external catheter and a canister coupled to a source of higher suction, e.g., a regulator at the hospital's suction line. That external catheter suction regulator is designed in such a way that it allows far greater flow at low pressures than do the traditional wall regulators. As such, it provides an efficient means for removing urine from a patient using an external catheter, wherein the flow rate is sufficiently high for increased effectiveness, yet is produced by a suction level that is sufficiently low to minimize the danger of injury to the delicate tissue of the patient adjacent the patient's urethral opening.

All of the references as cited herein are specifically incorporated by reference One aspect of the subject invention improves upon the inventions of our aforementioned earlier filed patent applications by providing external female catheters and suction regulators in integral units, which are simple in construction, low in cost, comfortable to use, and effective and safe in operation. Another aspect of the subject invention also improves upon the inventions of our aforementioned applications by providing stand-alone external female catheters which can be used in any system including a source of regulated suction, and which external female catheters are also simple in construction, low in cost, comfortable to use, effective and safe in operation.

SUMMARY OF THE INVENTION

One aspect of this invention is an external catheter configured for external disposition in fluid communication with a urethra opening of the female, whereupon urine voided by the female is received by the external catheter. The external catheter comprises a cover, an elongated suction tube and a malleable wire. The cover is formed of a liquid permeable material and is a self-supporting elongated member having a proximal end, a distal end and an elongated bore extending from an entryway opening at the proximal end to an interior point adjacent the distal end. The elongated suction tube has a proximal end and a distal end. The proximal end is configured to be coupled to a source of suction. The distal end has a single opening. The elongated suction tube is flexible and is configured to be introduced through the entryway opening for disposition within the bore of the cover, whereupon the single opening is located a predetermined distance from the interior point to result in a hollow chamber of a predetermined length within the cover. The hollow chamber is contiguous with the single opening and in fluid communication therewith, whereupon regulated suction from the suction source applied through the elongated suction tube to the chamber draws urine voided by the female through the cover into the chamber and from there through the elongated suction tube out of the proximal end of the suction tube for collection. The malleable wire extends along at least a portion of the elongated suction tube and is configured to be bent to enable the external catheter to be configured to a desired shape for comfortable disposition adjacent the urethra opening of the female.

In accordance with one preferred aspect of the external catheter of this invention, the external catheter includes a positioning member for ensuring that the single opening is located the predetermined distance from the interior point.

In accordance with another preferred aspect of the external catheter of this invention, positioning member comprises a stop on the elongated suction tube. The stop is configured to engage a first portion of the cover.

In accordance with another preferred aspect of the external catheter of this invention, the first portion of the cover comprises a recess located at the entryway opening.

In accordance with another preferred aspect of the external catheter of this invention, the elongated suction tube is a corrugated member having plural corrugations, with one of the plural corrugations forming the stop.

In accordance with another preferred aspect of the external catheter of this invention, the one of the plural corrugations has a larger cross-section than others of the plural corrugations.

In accordance with another preferred aspect of the external catheter of this invention, the recess is an annular recess.

In accordance with another preferred aspect of the external catheter of this invention, the malleable wire comprises an elongated member having a proximal end and a distal end. The proximal end of the malleable wire is configured to be located within a predetermined one of the corrugations, whereupon the distal end of the malleable wire is located adjacent the single opening.

In accordance with another preferred aspect of the external catheter of this invention, the malleable wire is the positioning member.

In accordance with another preferred aspect of the external catheter of this invention, the elongated suction tube is a corrugated member having plural corrugations and wherein the malleable wire comprises an elongated member having a proximal end and a distal end. The proximal end of the malleable wire is configured to be located within a predetermined one of the corrugations, whereupon the distal end of the malleable wire engages a portion of the cover at the interior point.

In accordance with another preferred aspect of the external catheter of this invention, the proximal end of the malleable wire is in the form of a ring and wherein the distal end of the malleable wire is of a general J-shape.

Another aspect of this invention is method for automatically removing by suction urine voided by a female patient. The method comprises providing an external female catheter comprising a cover, an elongated suction tube, and a malleable wire. The cover is formed of a liquid permeable material and is a self-supporting elongated member having a proximal end, a distal end and an elongated bore extending from an entryway opening at the proximal end to an interior point adjacent the distal end. The elongated suction tube is flexible and has a proximal end and a distal end. The proximal end of the elongated suction tube is configured to be coupled to a source of suction. The distal end of the elongated suction tube has a single opening. The malleable wire extends along at least a portion of the elongated suction tube and is configured to be bent. The elongated suction tube is introduced through the entryway opening for disposition within the bore of the cover, whereupon the single opening is located a predetermined distance from the interior point to result in a hollow chamber of a predetermined length within the cover. The hollow chamber is contiguous with the single opening and in fluid communication therewith. The malleable wire is bent to configure the external catheter to a desired shape for comfortable disposition adjacent the urethra opening of the female. The cover of the external catheter is disposed adjacent the urethra opening of the female. Regulated suction from a suction source is provided through the elongated suction tube to the chamber to draw urine voided by the female through the cover into the chamber and from there through the elongated suction tube out of the proximal end of the suction tube for collection.

In accordance with one preferred aspect of the method of this invention, the catheter includes a positioning member for ensuring that the single opening is located the predetermined distance from the interior point.

In accordance with another preferred aspect of the method of this invention, the positioning member comprises a stop on the elongated suction tube. The stop is configured to engage a first portion of the cover.

In accordance with another preferred aspect of the method of this invention, the first portion of the cover comprises a recess located at the entryway opening.

In accordance with another preferred aspect of the method of this invention, the elongated suction tube is a corrugated member having plural corrugations, with one of the plural corrugations forming the stop.

In accordance with another preferred aspect of the method of this invention, the one of the plural corrugations has a larger cross-section than others of the plural corrugations.

In accordance with another preferred aspect of the method of this invention, the malleable wire comprises an elongated member having a proximal end and a distal end. The proximal end of the malleable wire is configured to be located within a predetermined one of the corrugations, whereupon the distal end of the malleable wire is located adjacent the single opening In accordance with another preferred aspect of the method of this invention, the malleable wire is the positioning member.

In accordance with another preferred aspect of the method of this invention, the elongated suction tube is a corrugated member having plural corrugations and wherein the malleable wire comprises an elongated member having a proximal end and a distal end. The proximal end of the malleable wire is configured to be located within a predetermined one of the corrugations, whereupon the distal end of the malleable wire engages a portion of the cover at the interior point.

In accordance with another preferred aspect of the method of this invention, the proximal end of the malleable wire is in the form of a ring and wherein the distal end of the malleable wire is of a general J-shape.

DETAILED DESCRIPTION OF THE PREFERRED EMBODIMENT

Figures 1, 2:
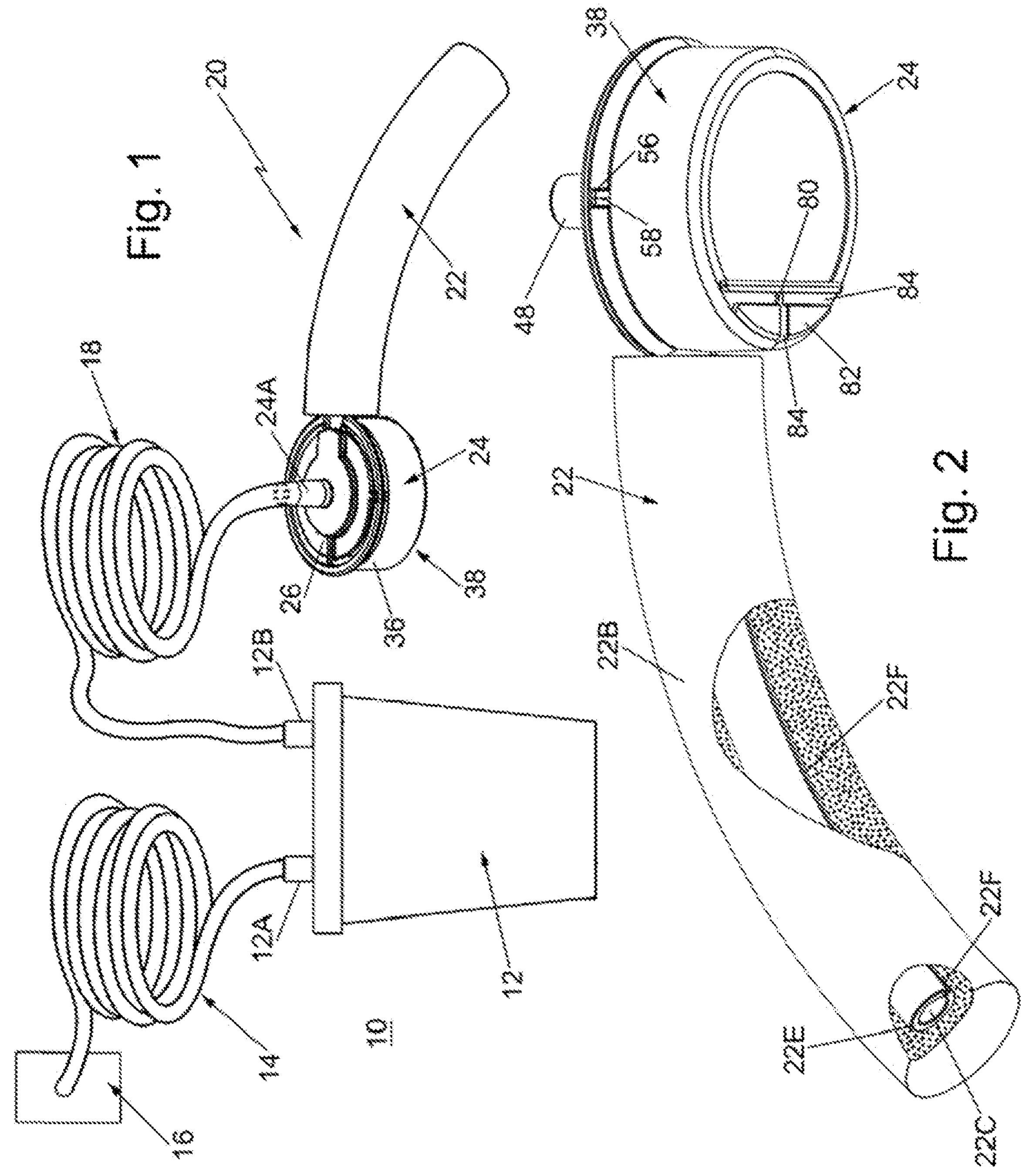
FIG. 1 is an illustration of one exemplary system for automatically removing urine from a female patient making use of an integrated unit having an external female catheter and suction regulator constructed in accordance with this invention and which can be used in a method of this invention.
FIG. 2 is an enlarged isometric view, partially in section, of the integrated external female catheter and suction regulator unit shown in FIG. 1.

Referring now to the various figures of the drawing wherein like reference characters refer to like parts, there is shown in FIG. 1 one exemplary embodiment of a system 10 including an integrated external female catheter and suction regulator unit 20 constructed in accordance with one exemplary preferred embodiment of this invention for automatically removing urine from a female patient.

The details of the integrated external female catheter and suction regulator unit 20 will be described later. Suffice it for now to state that the unit 20 basically comprises an external catheter 22 and a suction regulator 24 which when assembled together form an integrated (one-piece) unit. The external catheter 22 portion of the unit 20 basically comprises a suction tube 22A and a removable liquid permeable cover 22B. The cover 22B is disposed over and surrounding the suction tube 22A. When the unit 20 is in use the cover 22B placed against the urethra opening of a female patient to serve as a urine wicking member to receive urine which has been excreted by the patient. The suction regulator 24 portion of the unit 20 serves to provide a suitable safe regulated level of suction to the external catheter to effectively draw urine from the cover 22B through a longitudinally extending slot (to be described later) in the suction tube 22A into and through the suction regulator 24 to deliver it to a receptacle or canister 12, which forms a portion of the system 10.

The receptacle or canister 12 is of conventional construction and includes a port 12A that is configured to be connected, via a section of conventional tubing 14, to a suction source, e.g., a wall regulator 16 of the hospital's main suction line which provides suction to the suction regulator 24. The wall regulator 16 should be set to line vacuum or the maximum available vacuum pressure if a line function is not available. The canister 12 includes another port 12B, which is connected, via another section of conventional tubing 18, to a "line suction port" 24A, of the suction regulator 24. The suction regulator 24 includes another port, which is internal and hereinafter identified as the "regulated suction port" 24B, which is connected to and in fluid communication with the proximal end of a suction tube 22A.

As will also be described later the suction regulator 24 is configured to enable flow through it from the external catheter to the canister nearing the maximum the hospital's suction line or regulator 16 is capable of sustaining without allowing the pressure to rise above a desired operating value, e.g., 40 mmHg, of the suction regulator 24 in the event the external catheter becomes sealed against the patient. Since the suction regulator 24 is located between the external catheter 22 and the urine collecting canister or receptacle 12, the regulator 24 will be closer to the catheter 22 than if it was located between the canister or receptacle 12 and the hospital suction line or regulator 16, thereby enabling the maximum possible urine flow, but necessitates the urine flowing through the regulator. To that end, the entire unit 20 is intended to be a non-sterile, single-patient-use disposable unit.

Figure 7:
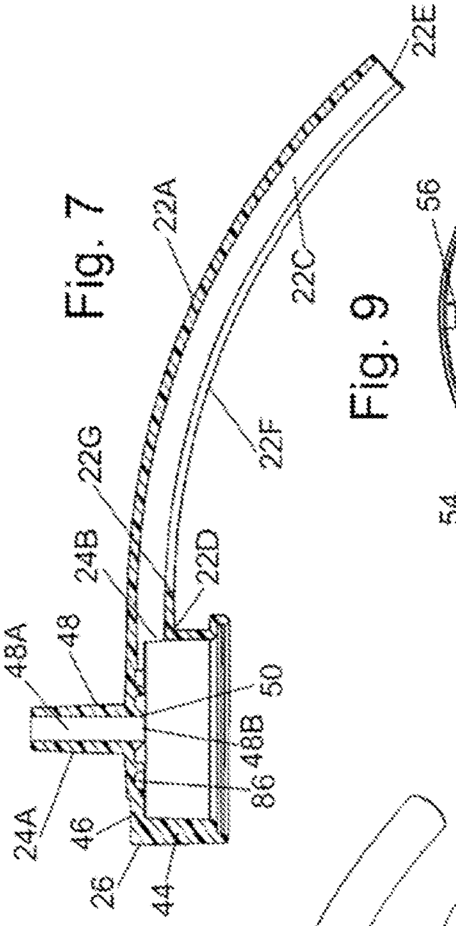
FIG. 7 is a reduced size longitudinal sectional view of one component, i.e., a body portion and an integrated suction tube, forming a portion of the integrated external female catheter and suction regulator unit shown in FIGS. 2 and 3.
Figure 8:
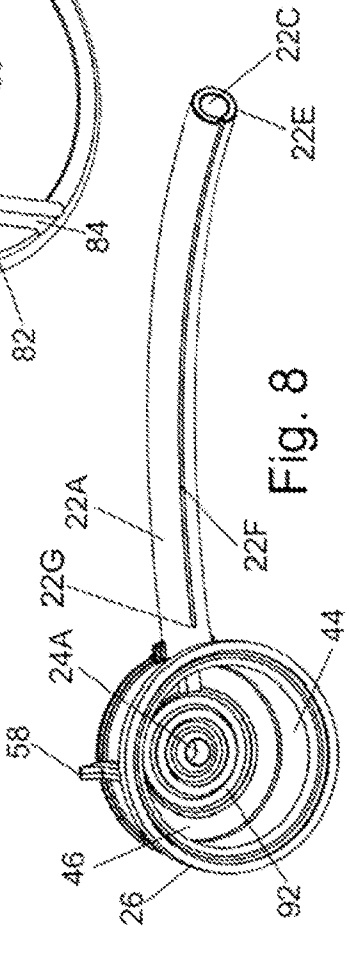
FIG. 8 is a reduced size isometric view of the component of the integrated external female catheter and suction regulator unit shown in FIG. 7.
Figure 6:
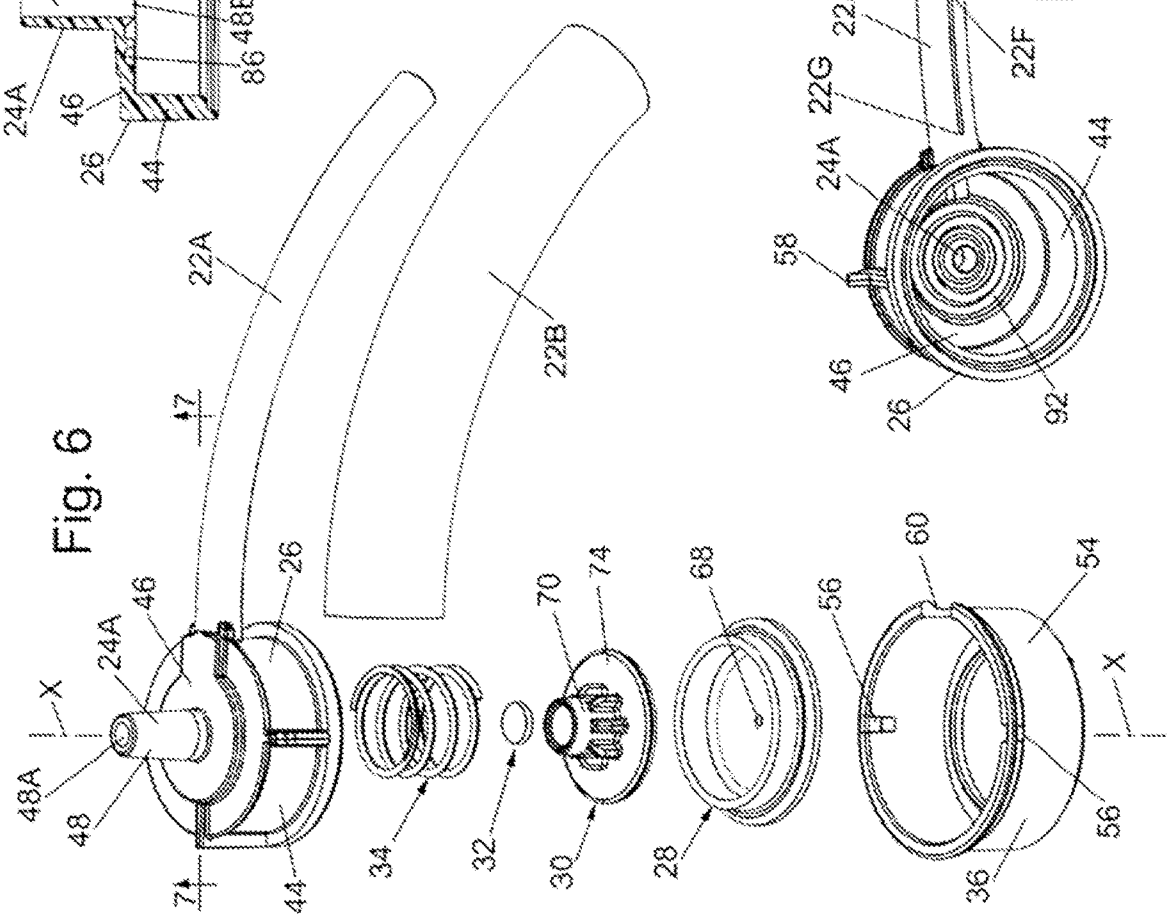
FIG. 6 is an exploded isometric view of the various components making up the integrated external female catheter and suction regulator unit shown in FIGS. 2 and 3.
Figure 12:
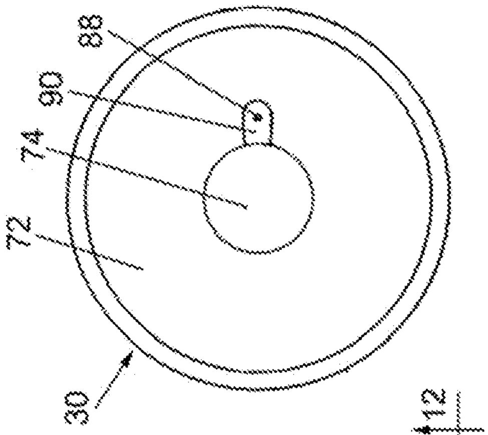
FIG. 12 is a reduced plan view taken along line 12-12 of FIG. 11.

Turning now to FIGS. 2, 3, 7 and 8, the details of the external catheter portion 22 will now be described. As mentioned above it basically comprises the suction tube 22A and the liquid permeable cover 22B. The suction tube 22A is an elongated arcuate member having a central passageway 22C extending the length thereof from its proximal end 22D to its distal end 22E. The distal end 22E is open. The proximal end 22D is also open and forms the heretofore identified internal port 24B (FIG. 3) of the suction regulator. The proximal end of the suction tube is secured to a portion of a housing assembly (to be described later) of the suction regulator. That portion of the housing assembly constitutes a hollow housing body 26. As best seen in FIGS. 7 and 8, the suction tube 22A includes a longitudinally extending slot 22F extending approximately the entire length thereof from a point 22G adjacent the housing body 26 to the distal end 22E. The slot is in fluid communication with the central passageway 22C of the suction tube 22 along the entire length of the slot. The portion of the suction tube 22A that includes the slot 22F constitutes a first or distal section of the suction tube, and the portion of the suction tube that is connected to the portion of the housing assembly constitutes a second or proximal section of the suction tube.

The cover 22B is a cylindrical member formed of a liquid permeable material, preferably one that is absorbent and hydrophilic, e.g., a polyurethane or a PVA (polyvinyl alcohol) sponge, although it could be formed of other liquid permeable materials such as, cellulose, polyurethane, gauze, etc. As best seen in FIG. 2 the cover 22B includes a central passageway extending from its proximal end to a point adjacent its distal end. The internal diameter of the central passageway of the cover 22B is approximately the same size or slightly smaller than the external diameter of the suction tube 22A so that the suction tube can be located therein, with the cover held thereon by friction, whereupon the closed distal end of the cover closes the open distal end 22E of the suction tube. Moreover, the cover extends the entire length of the suction tube up to a point immediately adjacent the housing body 26. Accordingly, when regulated suction produced by the suction regulator 24 (as will be described later) is applied at the port 24B that regulated suction will appear along the length of the slot 22F to draw any urine that the female patient voided into the cover from there into the slot whereupon that urine will be pulled into the passageway 22C and carried by air from through that passageway to the suction regulator 24. From there the urine is carried to the receptacle or canister 12. In particular, with the system 10 as described above when suction is applied from the hospital's suction line or wall regulator 16, that high level of suction is conveyed through the tubing section 14, from whence it is applied to the canister or receptacle 12 and the associated tubing section 18 to the line suction port 24A of the suction regulator 24, whereupon it is regulated (e.g., reduced) by operation of the suction regulator to a much lower operating level, e.g., 40 mmHg. That reduced or regulated suction will appear on the suction port 24B of the regulator 24 and from there to the external catheter 22 to thereby draw urine from the external catheter 22 back through the regulator 24, and out through the tubing section 18 into the receptacle or canister 12 for collection therein.

It should be noted that for many applications the operating level is preferably approximately 40 mmHg. However, that level could be raised up to approximately 60 mmHg, since some hospitals are comfortable with higher vacuum pressures. If desired the system 10 may also include an overflow detector of any suitable construction to provide an indication that the amount of urine within receptacle has reached a predetermined threshold, e.g., is about to overflow, and/or to provide a signal to a controller (not shown) stop to halt the operation of the system so that no further urine is drawn into the receptacle until it can be emptied. For example, the canister 12 may include a shut off float valve and/or a filter at outlet 12A to prevent possible contamination of the hospital's main suction.

As should be appreciated by those skilled in the art from the discussion to follow the operation of the suction regulator 24 ensures that a desired level of suction is applied to the external catheter 22 to ensure proper and safe operation of the system, i.e., to maximize the rate at which urine may be withdrawn from the catheter into the receptacle or canister without subjecting the delicate tissue of the woman at her urethra opening to injury, e.g., a hematoma, from excess suction thereat.

Figures 3, 4, 5:
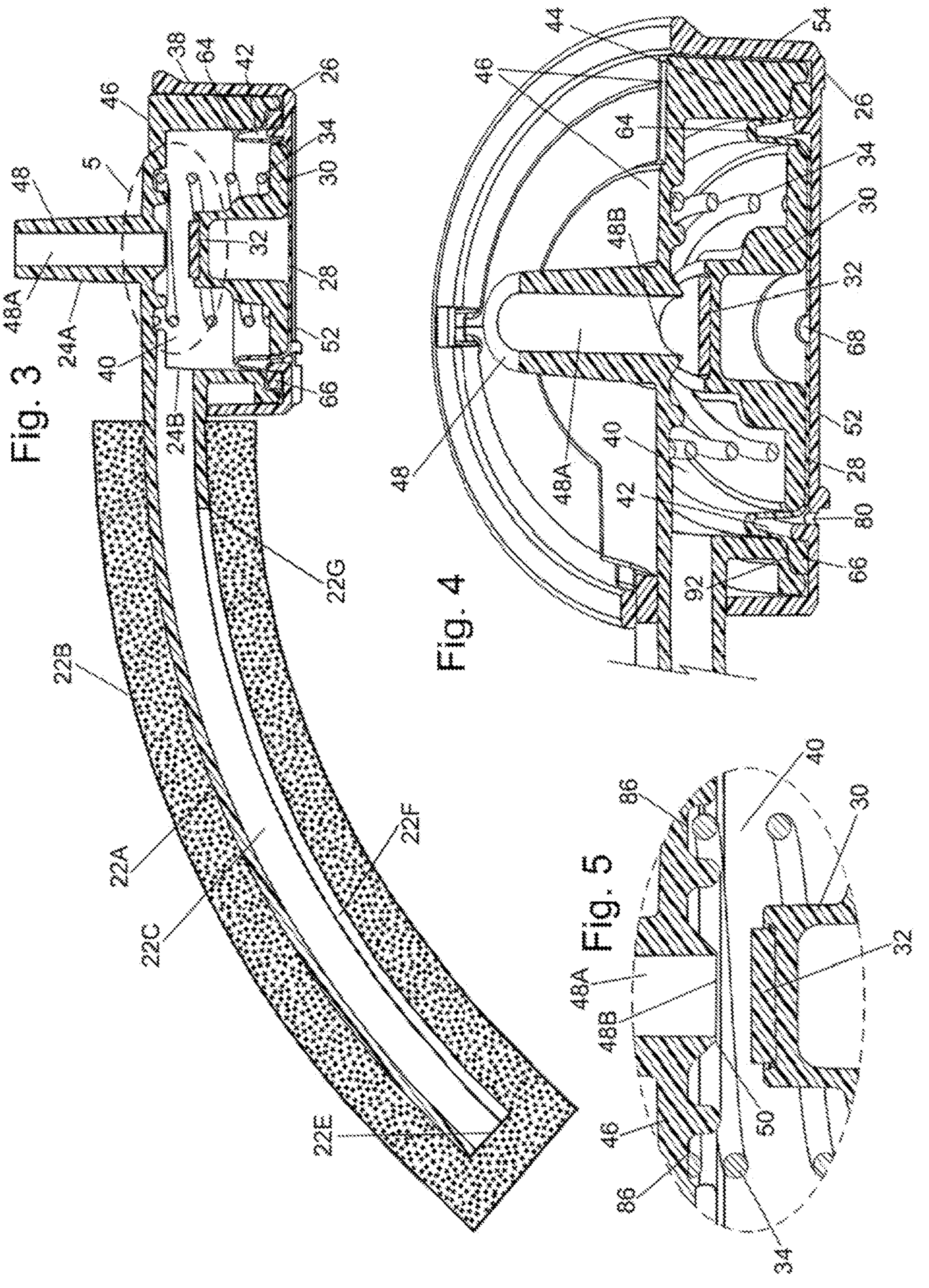
FIG. 3 is an enlarged longitudinal sectional view of the integrated external female catheter and suction regulator unit shown in FIG. 2.
FIG. 4 is an enlarged sectional view of the suction regulator portion of the integrated external female catheter and suction regulator unit shown in FIGS. 2 and 3.
FIG. 5 is an enlarged sectional view of the portion of the suction regulator shown within the area designated by the broken line oval designated by the reference number 5 in FIG. 3.
Figure 16:
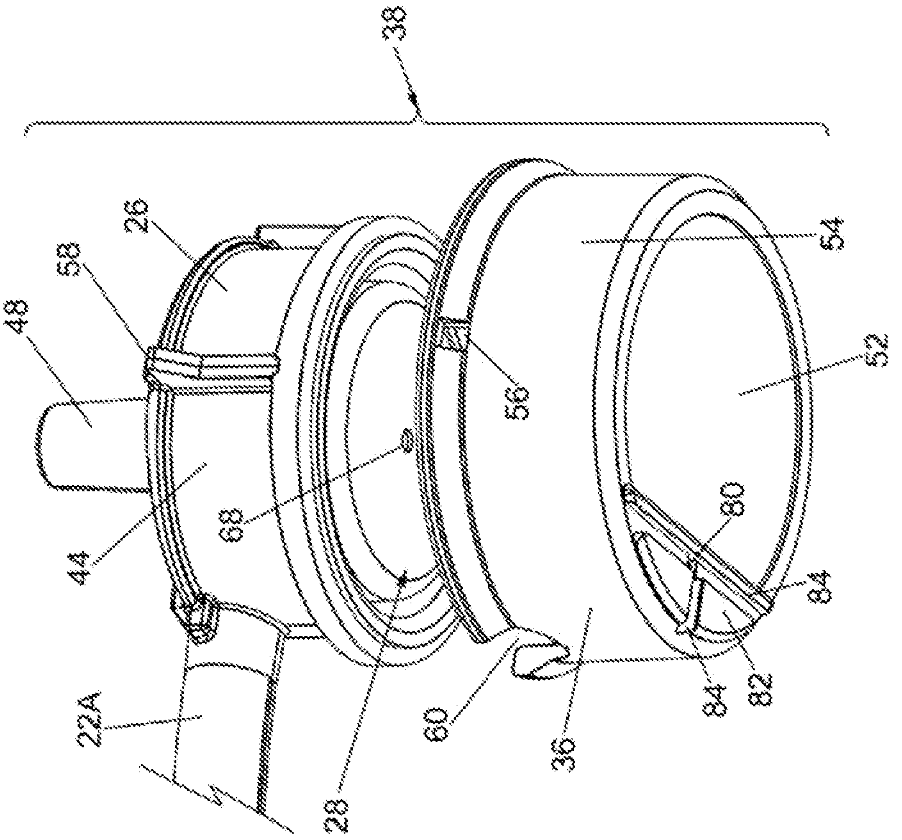
FIG. 16 is an enlarged isometric view showing the assembly of the cap member of FIG. 9 to the body portion and integrated suction tube component of FIGS. 7 and 8 to complete the assembly of the integrated external female catheter and suction regulator unit shown in FIGS. 2 and 3.

Turning now to FIGS. 3-6, the construction of the suction regulator portion 24 of the unit 20 will now be described. To that end as can be seen the suction regulator 24 basically comprises a flexible diaphragm 28, a piston 30, a sealing disk 32, a helical compression spring 34, and a housing assembly 38. The housing assembly 38 is made up of the heretofore identified housing body 26 and a lid or cover 36. The lid or cover 36 and the housing body 26 are configured to be connected together, as will be described later and as shown in FIG. 16, to form the hollow housing assembly 38. That assembly encloses (houses) the other components making up the suction regulator 24. The housing body 26 and the cover 36 are preferably formed of a rigid plastic, such as ABS, although other plastics can be used. The suction tube 22A, being integral with the housing body 26 is also formed of the same material as the housing body, but could be formed of some other material. That other material may be chosen to exhibit some degree of flexibility to enhance engagement of the external catheter 22 with the portion of the female's body contiguous with her urethra opening As best seen in FIGS. 3-8 the housing assembly 38 defines two internal chambers, namely, an upper chamber 40 and a lower chamber 42, which are separated from each other by a portion of the diaphragm 28. The housing body 26 includes a circular annular sidewall 44 projecting downward from a top wall 46. The circular sidewall 44 extends about a central axis X (FIG. 6) of the suction regulator. A tubular extension 48 extends upward from the top wall and centered on the axis X. The tubular extension forms the heretofore identified line suction port 24A and includes a passageway 48A extending through it. The lower end of the passageway 48A is open at 44B, with the portion of the top wall 46 contiguous with the opening 48B forming a beveled or conical surface valve seat 50 (FIG. 5). The opening 44B is in fluid communication with the upper chamber 40 in the interior of the housing assembly 38 of the suction regulator 24. The upper or free end of the passageway 48A is open and configured so that the distal end of the tubing section 18 can be connected to it, whereupon the passageway extending through that tubing section will be in fluid communication with interior of the housing assembly 38 and with upper chamber 40.

Figure 9:
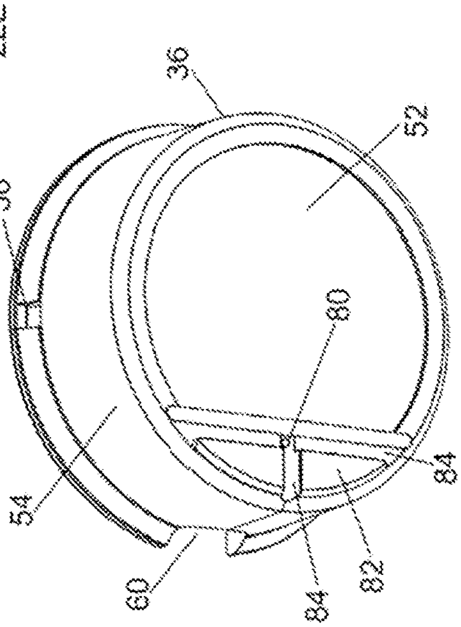
FIG. 9 is an enlarged isometric view of another component, i.e., a cap member, of the integrated external female catheter and suction regulator unit shown in FIGS. 2 and 3.

The lid or cover 36 is a generally cup-shaped member having a generally planar bottom wall 52 and a circular annular sidewall 54 projecting upward therefrom. The sidewall 54 includes a pair of diametrically opposed notches 56 immediately adjacent the lower edge of the sidewall. As can be seen in FIG. 16 the notches 56 are configured to receive respective diametrically opposed projecting tabs 58 of the housing body 26 to secure the lid or cover 36 to the housing body 26 and thus complete the housing assembly 38. The sidewall 54 of the lid or cover 36 also includes an arcuate recess 60 (FIG. 9) in the edge of the sidewall located midway between the notches 56. The recess 60 serves to receive the suction tube 22A when the lid or cover 36 is secured to the housing body 26.

Figure 15:
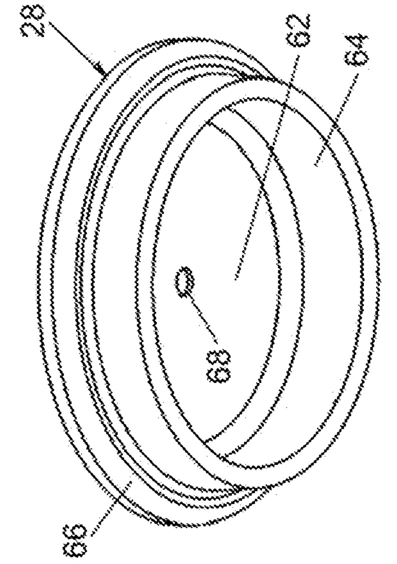
FIG. 15 is an enlarged isometric view of the diaphragm of FIG. 14 but taken from a different angle.
Figure 14:
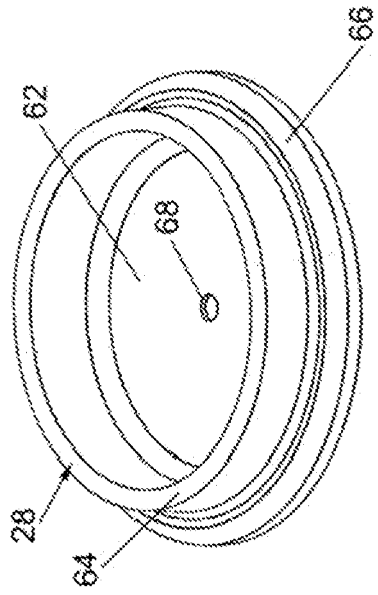
FIG. 14 is an enlarged isometric view of another component, i.e., a diaphragm, of the integrated external catheter and suction regulator unit shown in FIGS. 2 and 3.
Figure 13:
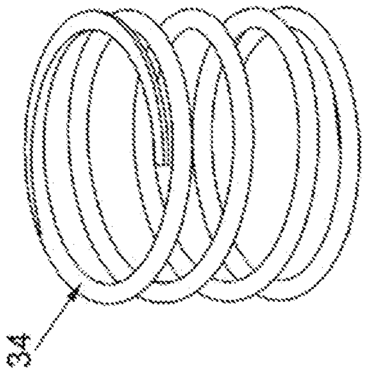
FIG. 13 is an enlarged isometric view of another component, i.e., a biasing spring, of the integrated external female catheter and suction regulator unit shown in FIGS. 2 and 3.

The diaphragm 28 is best seen in FIGS. 14 and 15, and is preferably a rolling diaphragm formed of any resilient flexible material, e.g., silicone, nitrile, etc. The diaphragm includes a generally planar circular central portion 62 and a folded generally V-shaped or U-shaped edge portion 64 surrounding the central portion and terminating in a flanged generally planar thickened periphery 66. A small opening or hole 68 is located in the center of the central portion 62. The central portion 62 is disposed on a planar top surface of the piston 30 (to be described later), with the thickened periphery 66 of the diaphragm disposed on an annular ledge 92 (FIG. 4) at the lower end of the sidewall 44 of the housing body 26 between that ledge and the inner surface of the bottom wall of the lid or cover 36. With the lid or cover secured to the housing base 26 the thickened periphery 66 of the diaphragm 28 is tightly sandwiched between the ledge and the inner surface of the lid or cover. This arrangement divides the interior of the suction regulator into the heretofore identified upper chamber 40 and lower chamber 42. In particular, the upper chamber is formed between the inner surface of the top wall 46 of the body member 26, the contiguous inner surface of the sidewall 44 of the body member, the upper surface of a portion of the diaphragm 28 and a portion of the piston 30. The lower chamber 42 is formed between the inner surface of bottom wall 52 of the lid or cover 36, and the central portion 62 and contiguous V or U-shaped portion 64 of the diaphragm 28.

Figure 11:
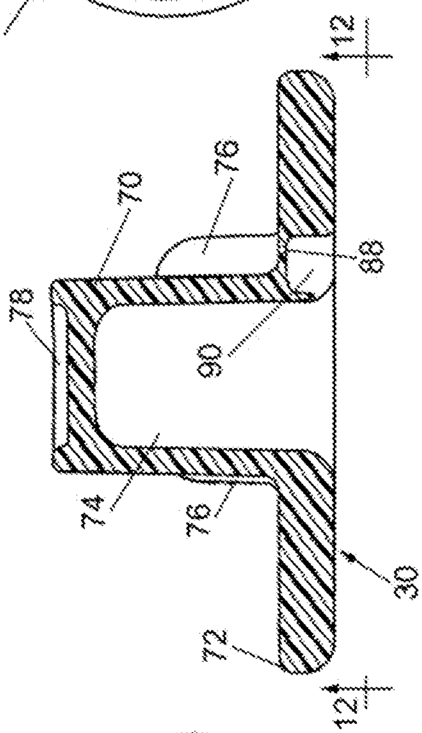
FIG. 11 is a sectional view taken along line 11-11 of FIG. 10.
Figure 10:
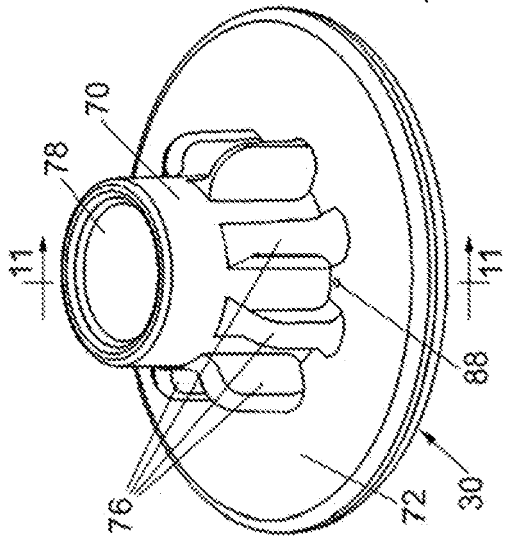
FIG. 10 is an enlarged isometric view of another component, i.e., a piston, of the integrated external female catheter and suction regulator unit shown in FIGS. 2 and 3.

The piston 30 is best seen in FIGS. 10 and 11 and basically comprises a unitary body formed of a rigid plastic, such as ABS. The body includes a central hub 70 whose bottom end terminates in a circular flange 72. The bottom surface of the flange is planar, but includes a circular recess 74 in the center thereof and extending into the hub 70. A plurality of ribs 76 extend outward radially from the hub and serve to reinforce the flange 72 and to center the biasing spring 34 about the central axis X. The top surface of the hub 70 includes a recess 78 for receipt of the sealing disk 32.

The sealing disk 32 is fixedly secured in the recess 78 of the piston 30 and serves as a valve member to engage the valve seat 50 in the upper chamber 40 when excess suction is applied (as will be described later). The sealing disk 32 is formed of any suitable material, e.g., silicone rubber.

The cover or lid 36 includes a small opening or vent (FIGS. 2, 4, 9 and 15) to the ambient atmosphere which will be referred to as the "atmospheric reference port" 80. The atmospheric reference port ensures that the lower chamber 42 will be at the pressure of the ambient atmosphere. In particular, the port 80 extends through the thickness of the cover and is in fluid communication with the interior of lower chamber 42 to maintain that chamber at atmospheric pressure. Inasmuch as the atmospheric reference port 80 is located in the bottom surface of the cover 36, it is susceptible to being blocked or covered by a sticker, some other object or even a portion of the female's body. To prevent such an occurrence the lid or cover is shaped to prevent blockage of the port 80. In particular, the lid or cover includes a thickened portion 82 located adjacent the port 80 with an elongated shallow tripartite or T-shaped recess or slot 84 extending into the thickened portion. The outer edge of the atmospheric reference port 80 is located at the bottom of the slot 84 at the intersection of the slot's various three sections and is in fluid communication with each of those sections. The outer end of each of the slot sections is open. Thus, if something should be on the surface of the thickened portion 82 of the lid or cover disposed over the atmospheric reference port 80 air can still enter into that port via any open end of the T-shaped slot 84.

A label (not shown) bearing indicia or information regarding the unit 20 may be fixedly secured within a very shallow recess 96 in the outer surface of the lid or cover adjacent the thickened portion 82 so its presence does not block the T-shaped slot 84.

The biasing spring 34 is a helical compression spring formed of any suitable material, e.g., stainless steel. As best seen in FIGS. 3-6 and 13, the spring is located within the upper chamber 40, with the lower end of the spring in engagement with the undersurface of the flanged portion 72 of the piston 30 and surrounding a piston's central hub 70 and with the upper end of the spring located within an annular recess 86 (FIG. 5) in the undersurface of the top wall 46 of the housing body 26. The spring is under compression to bias the piston and diaphragm downward and away from the valve seat 50.

As mentioned above, the suction regulator 24 regulates the level of suction to a desired operating value, e.g., 40 mmHg, and provides the regulated suction to the external catheter (the urine wicking member) 22. To that end, the regulator 24 is configured to limit the amount of suction applied to the external catheter to that desired value even if a level of suction greater than that predetermined value is applied to the suction regulator from the suction source (particularly if the suction source is at a much higher level, which will typically be the case if the suction source is the hospital's suction line). The predetermined or desired suction value (hereinafter referred to has the "regulator's set-point" or "regulated set-point value") is fixed and is factory-established by the spring 34 and dimensions of the housing body 26, the cover or lid 36, the piston 34 and the sealing disk 42. In this regard the pressure within the lower chamber 42 will be equal to atmospheric pressure by virtue of the communication of that chamber with the ambient atmosphere via the atmospheric reference port 80. With suction applied, the pressure within the upper chamber 40 will be lower than the atmospheric pressure within the lower chamber 42. The differential pressure between the chambers 40 and 42 will force the diaphragm 28 and the piston 30 upward toward the valve seat 50. The compression spring 34, however, will impart a counter force on the piston and diaphragm that opposes the differential pressure force, thereby forcing the piston upward such that the level of suction appearing at the regulated suction port 24B is the desired operating value, e.g., 40 mmHg.

If the suction applied via line suction port 24A is greater that the predetermined value or level the piston 30 and diaphragm 28 will move such that the sealing disk 32 on the piston's hub 70 comes into engagement with the valve seat 50, thereby isolating the upper chamber 40 from the suction appearing on the line suction port 24A. This action thereby limits the level of suction in upper chamber and hence at external catheter 22 to the predetermined level (operating value). If, however, the suction applied via line suction port 24A is less than the predetermined operating level the piston and diaphragm will only move part of the way downward. As such the level of suction applied to the line suction port 24A will equal that in the regulated suction port 24B and that applied to the external catheter 22.

It should be pointed out at this juncture that the suction regulator 26 is also configured to prevent the sealing disk 32 on the piston from becoming stuck for an extended period of time on the valve seat 50 in the event of what will be referred to hereinafter as an "over-travel situation". In this regard, if the suction regulator 24 is operated in a manner such that a high level of suction is applied very rapidly, the piston may experience an over-travel situation wherein it moves upward very quickly such that the sealing disk 32 becomes stuck on the valve seat 50. Under this condition the suction applied to the suction tube 24A of the external catheter would be at a higher level than the suction regulator 24 was set to provide, e.g., 40 mmHg. The suction regulator could thus stay in that state for an extended/indefinite period of time, particularly if the external catheter becomes blocked, e.g., its wicking portion (the sponge cover 24B) is in tight engagement with the vaginal tissue surrounding the urethral opening and not over the urethral opening itself. To prevent such an occurrence, the regulator 24 includes two "bleed" holes. One bleed hole is the heretofore-identified small hole 68 located in the center of the diaphragm 28. The second bleed hole is identified by the reference number 88 and is located in the piston 30. In particular, as best seen in FIG. 11A, the cylindrical cavity 74 in the piston contiguous with the bottom surface of the flanged portion 72 includes a radially extending recess 90. The bleed hole 88 is located in that recess and extends through the flanged portion of the piston. Since the bleed hole 68 in the diaphragm 28 is located in the center thereof, i.e., on the central axis X, it will overlie and be in fluid communication with the cylindrical cavity 74 in the piston. The recess 90 is in fluid communication with the cylindrical cavity 74. Thus, the bleed hole 88 in the piston will be in fluid communication with the bleed hole 68 in the diaphragm. Since the bleed hole 68 in the diaphragm is in communication with the lower chamber 42, that chamber will be in fluid communication with the upper chamber 40 via the communicating bleed holes 68 and 88. Hence, if the sealing disk 34 on the piston should become stuck on the valve seat 50, air which enters into the lower chamber 42 via the atmospheric reference port 80 can then pass through the bleed hole 88 into the cylindrical cavity 74, and from there through recess 90 into the bleed hole 88, from whence it will enter into the upper chamber 40. The ingress of air into the upper chamber will decrease the vacuum within that chamber, thus enabling the spring 34 to move the piston 30 downward so that the sealing disk 32 is off of the valve seat 50.

It must be pointed out at this juncture that the sealing disk 32 becoming stuck on the valve seat 50 may not be an issue. In such a case the diaphragm 28 need not include the bleed hole 68, and the piston 30 need not include the bleed hole 88 and the associated recess 90.

In accordance with one exemplary preferred embodiment of the suction regulator 24, inner diameter of the lower chamber 42 is approximately 1.5 inch. The inner diameter of the upper chamber 40 is approximately 1.5 inch. The spring is configured to naturally apply a bias force of approximately 1.0 pound. The inner diameter of the passageway 48A is approximately 0.25 inch. The opening 48B located within the bounds of the valve seat 50 is approximately 0.22 inch. The atmospheric reference port 80 is approximately 0.035 inch in diameter. The bleed hole 88 is approximately 0.016 inch in diameter. The bleed hole 68 is approximately 0.062 inch in diameter. Each tubing section 14 and 18 is conventional having an internal passageway of approximately 0.25 inch in diameter, and each section is approximately six feet in length, but could be shorter or longer depending upon the application. In any case with an integrated external female catheter and suction regulator unit 20 sized as just described, in a system like that described during typical operation the flow rate of air into the upper chamber 40 via bleed holes should be in the range of approximately 3 to 10 standard cubic feet per hour (SCFH). In fact, benchtop testing suggests that one version of the system 20 of this invention, making use of its disposable regulator 26 is capable of air flow rates up to 100 SCFH as compared to the 15 SCFH rate observed with some commercially available wall regulator set to the suggested 40 mmHg. The additional flow allows for increased urine capture at the interface of the actual catheter, faster drying of the catheter (which helps prevent skin breakdown and infection) and pulls the urine through the tubing into the canister 30 more efficiently. This is especially true if the tubing drapes down below the height of the patient and canister.

The integrated external female catheter and suction regulator unit 20 of this invention is designed for use with a single female patient over a prolonged period of time and after use with that patient, it is to be disposed. The cover 22B is however designed to be replaced on the suction tube whenever necessary for that particular patient. To replace the cover 22B, all that is required is to remove the used cover from the suction tube 22A by pulling it in the distal direction and then replacing the used (soiled) cover with a fresh cover on the suction tube.

Figures 17, 18, 19:
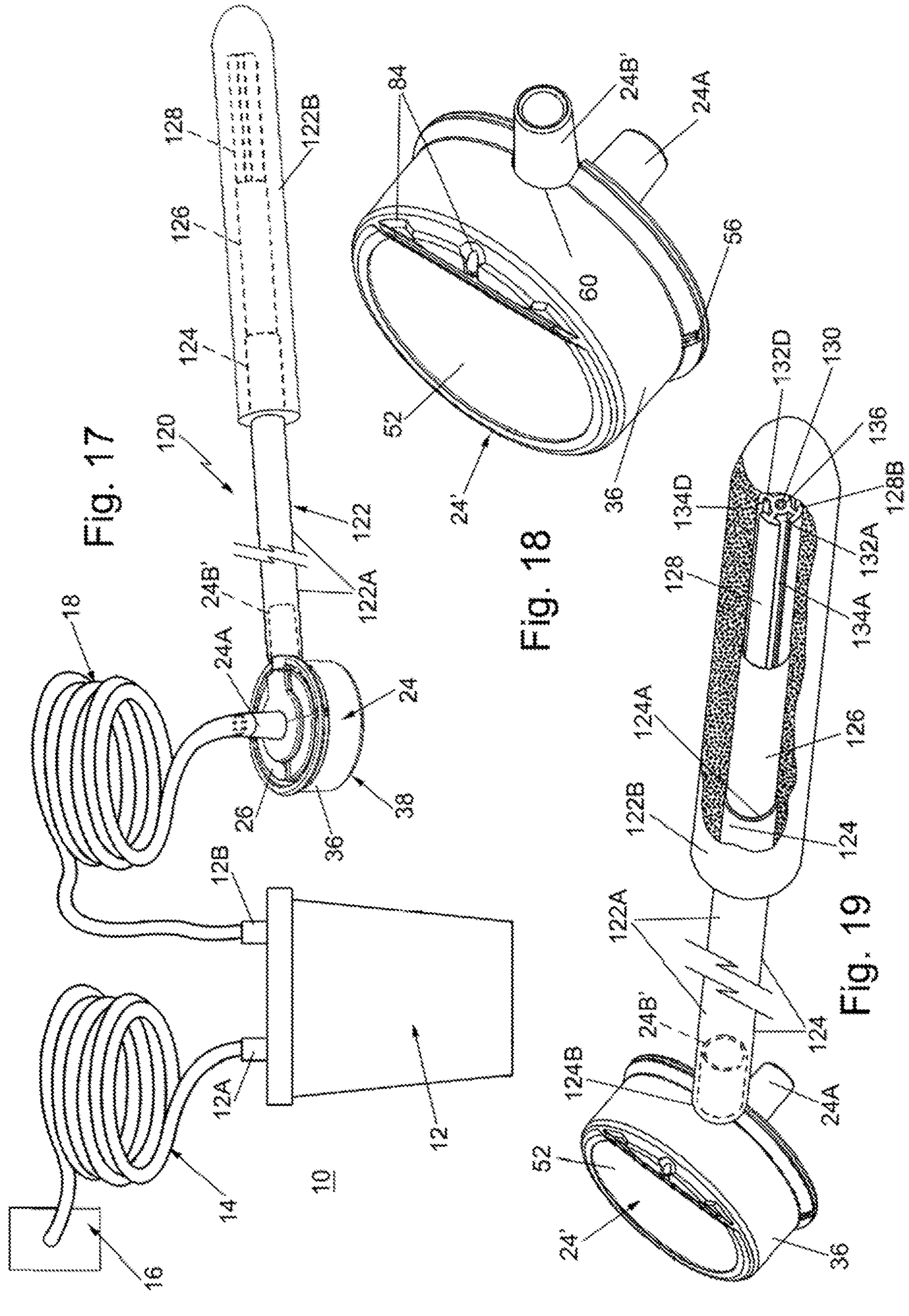
FIG. 17 is an illustration, similar to FIG. 1, but showing another exemplary system for automatically removing urine from a female patient making use of a more preferred integrated unit having an external female catheter and suction regulator constructed in accordance with this invention and which can be used in a method of this invention.
FIG. 18 is an isometric view of an alternative suction regulator forming a portion of the more preferred integrated unit shown in FIG. 17.
FIG. 19 is an enlarged isometric view, partially in section, of the integrated external female catheter and suction regulator unit shown in FIG. 17.

Turning now to FIG. 17 there is shown another and more preferred exemplary system 10' for automatically removing urine from a female patient making use of a more preferred integrated unit 120 having an external female catheter 122 and suction regulator 24' constructed in accordance with this invention and which can be used in a method of this invention.

Figure 20:
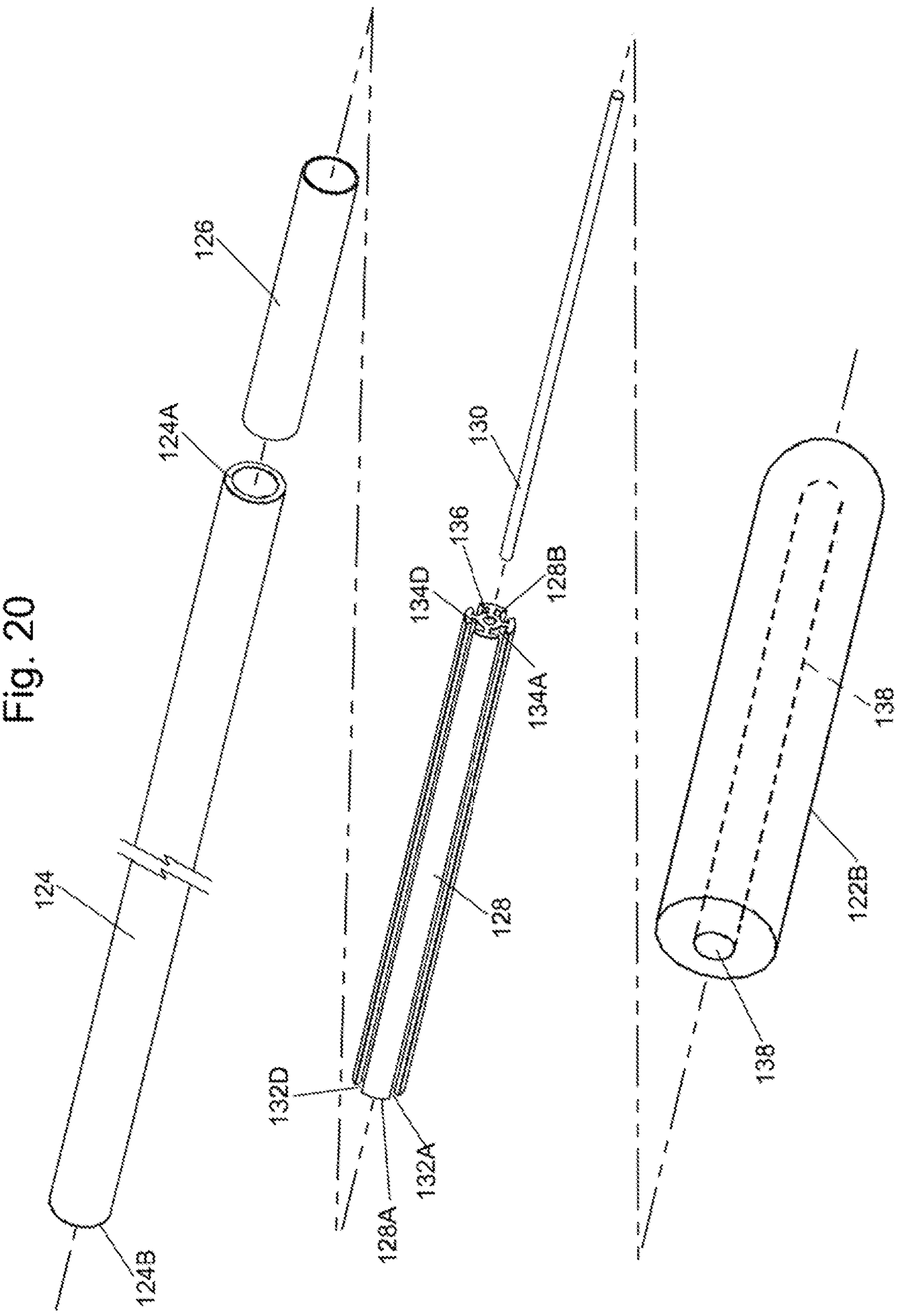
FIG. 20 is an enlarged exploded isometric view of another portion of the integrated external female catheter and suction regulator unit shown in FIG. 17.

The system 10' is identical to the system 10 except for the construction of the integrated unit 120, and in particular the suction regulator 24' and the external female catheter 122. The components of the system 10' which are common to the system 10 will be given the same reference numbers and the details of their construction, arrangement and operation will not be reiterated in the interest of brevity. The suction regulator 24' is identical in construction to the suction regulator 24 except that the regulated suction port 24B terminates in a tubular connector 24B'. The tubular connector 24B' is best seen in FIGS. 17 and 18 and is configured to receive the proximal end of a tubing section of the external female catheter 122 so that the regulated suction produced by the suction regulator is applied to the external female catheter. The external female catheter 122 is best seen in FIGS. 17 and 19 and basically comprises an elongated suction tube 122A and a removable liquid permeable cover 122B. The elongated suction tube 122A is best seen in FIGS. 19 and 20 and basically comprises an assembly of an elongated flexible conduit or tubing section 124, an optional cover tube 126, a multi-slot end-piece 128, and a section of malleable wire 130.

The conduit or tube 124 is a section of conventional tubing formed of any suitable flexible material, e.g., flexible PVC tubing, like used in hospitals to carry fluids via suction and has a distal end 124A and a proximal end 124B. The proximal end 124B of the tubing section 124 receives the tubular connector 24B' of the suction regulator 24' to thereby connect the elongated suction tube 122A to the suction regulator. The distal end 124A of the tubing section 124 receives the proximal end 128A of the multi-slot end-piece 128.

The removable liquid permeable cover 122B is in the form of a cylindrical sponge-like body having a rounded or domed distal end. The cover 122B will be described in detail later. Suffice it for now to state that that in one exemplary preferred embodiment of this invention the cover 122B is approximately 5.75 inches long measured from its distal end to its proximal end and has an outside diameter of approximately 1.125 inches. The cover is mounted on the distal end portion of the elongated suction tube 122A and overlies approximately the distal-most 5 inches of the elongated suction tube. In particular, the cover is mounted on and over the distal end 124A of the tubing section 124 and on and over the cover tube 126 and the multi-slot end-piece 128, with the proximal portion of the cover overlying approximately 0.5 inch of the tubing section 124 to ensure an air-tight seal.

The multi-slot end-piece 128 forms a first section of the elongated suction tube and is a flexible rod-like member, e.g., an extrusion of any suitable flexible material, e.g., polyurethane. In the exemplary embodiment shown the end-piece is approximately 5 inches long with an outside diameter of approximately 0.425 inch. The end-piece 128 has a generally circular profile in cross-section (see FIG. 21) and includes plural longitudinally extending passageways or channels 132A, 132B, 132C and 132D, which run the full length to the end-piece. The passageways are equidistantly spaced about the periphery of the end-piece and each passageway includes a narrow width, e.g., 0.1 inch, longitudinally extending slot at the surface of the periphery of the end-piece. In particular, the passageway 132A includes an associated slot 134A, the passageway 132B includes an associated slot 134B, the passageway 132C includes an associated slot 134C, and the passageway 132D includes an associated slot 134D. The proximal end of each of the passageways 134A-134D is open, as is the distal end of each of those passageways. A short length, e.g., 0.5 inch, of the proximal end of the end-piece 124 is disposed within the distal end 124A of the tubing section 124. The tubing section 124 from the proximal end of the end-piece to the connector 24B' of the suction regulator 24' forms what can be called a second section of the suction tube 122A.

The optional cover tube 126 is a section of heat shrinkable tubing, which is disposed over the portion of the end-piece 128 immediately adjacent the distal end 124A of the tubing section 124, thereby covering or closing off the underlying proximal portions of the slots 134A-134D, but leaving approximately 40 mm of the distal end portions of the slots uncovered or exposed. Thus, when the proximal end of the end-piece 128 is disposed within the distal end 124A of the tubing section 124 and the heat shrinkable cover tube 126 is in place, the regulated suction applied from the suction regulator to the tubing section 124 will be applied to the open proximal end of each of the passageways 132A-132D down the length of the passageways to exit the uncovered portions of the slots 134A-134D, respectively, and the open distal ends of those passageways.

It should be noted that while the exemplary embodiment shown and described above includes four passageways and four associated slots, it is contemplated that the end-piece can have any number of passageways, with associated slots, e.g., three passageways and three associated slots. The key feature being that the slots are directed in different, equidistantly spaced radial directions with respect to the central longitudinal axis of the end piece. As such irrespective of the orientation of the elongated external catheter about its central longitudinal axis with respect to the urethra opening of the patient, there will be at least one slot generally directed to the urethra opening to accept urine therefrom. Moreover, the distal end of each of the passageways 134A-134D is open. Thus, when the external female catheter is disposed adjacent the urethra of the patient, and regulated suction applied to it from the suction regulator, the regulated suction is applied to the distal end portion of the cover 122B, i.e., the distal portions of the slots 134A-134D that are not covered by the cover tube 126. That action draws urine from the patient through the distal portion of the cover 122B into the exposed portions of the slots 134A-134D and the open distal ends of the passageways 132A-132D and from there through those passageways into the tubing section 124 and from there through the suction regulator 24' to the collection canister 12. The use of multiple channels facilitates the removal of urine while minimizing the chance that the channels will be collapsed by portions of the patient's anatomy.

Figure 21:
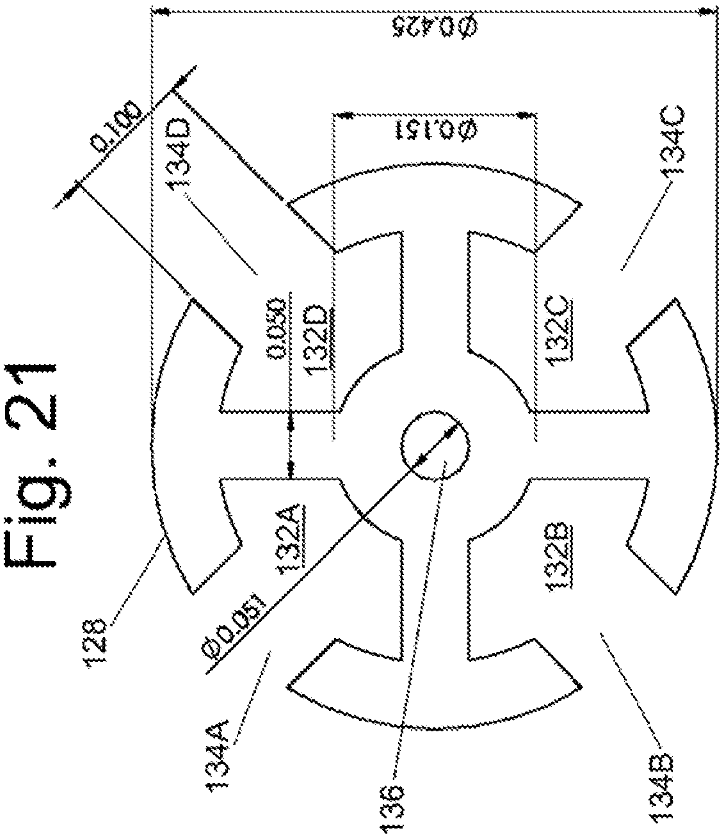
FIG. 21 is a greatly enlarged end view of one of the components, i.e., a multi-slot end-piece, making up a portion of the integrated external female catheter and suction regulator unit shown in FIG. 17.
Figure 22:
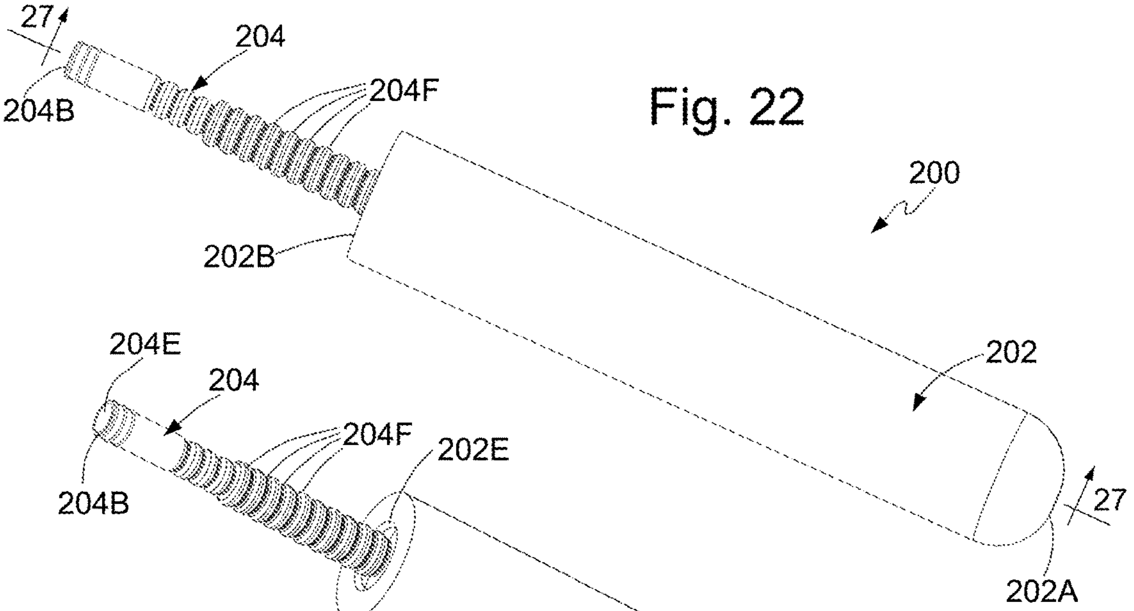
FIG. 22 is plan view of one exemplary embodiment of an external female catheter constructed in accordance with one aspect of this invention and which external female catheter is configured to be connected to any source of regulated suction.
Figure 23:
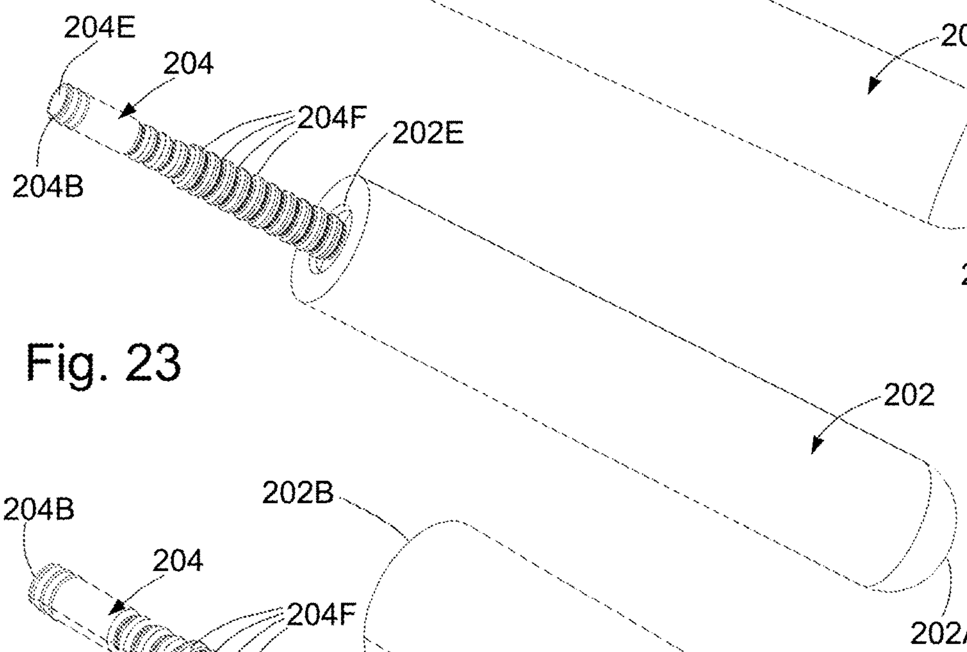
FIG. 23 is an isometric view of the external female catheter of FIG. 22.

As best seen in FIGS. 18 and 21 the end-piece 128 includes a small diameter, e.g., 0.051 inch, central passageway 136 in which the malleable wire 130 is located. The malleable wire can be formed of any suitable material, e.g., stainless steel, aluminum, provided that it is biocompatible and can be readily bent into a desired shape and will hold that shape. With the wire 130 located in the passageway 136 and the cover 122B mounted on the distal portion of the elongated suction tube 122A, the end-piece 128 can be bent into a somewhat arcuate shape, so that the cover 122B conforms closely and comfortably to the anatomy of the patient contiguous with the patient's urethra opening. Other dimensions of the end-piece 128 are shown in FIG. 21.

Turning now to FIG. 18, the details of the cover 122B will now be described. In particular as mentioned earlier the cover 122B is a cylindrical member whose distal end or tip is rounded or domed and is approximately 5.75 inch in length, and with a 1.125 inch outside diameter. The cover includes a central passageway 138 extending from its proximal end to a point closely adjacent its distal end. The inside diameter of the passageway 138 is approximately 0.375 inch. The thickness of the rounded tip is approximately 0.375 inch. The passageway 138 is configured for receipt of the end-piece 128, the optional cover tube 126, and the distal end portion of the tubing section 124. To that end the internal diameter of the central passageway of the cover 122B is slightly smaller than the external diameter of the end-piece 128 so that the cover 122B is held thereon by friction. With the cover in place, the closed distal end of the cover overlies the open distal ends of the passageways 134A-134D of the end-piece 128.

The cover is formed of a liquid-permeable material, e.g., hydrophilic polyurethane foam, although it could be formed of other liquid permeable hydrophilic materials such as PVA (polyvinyl alcohol) sponge, cellulose, etc. One preferred exemplary embodiment of a hydrophilic polyurethane foam cover is a hybrid foam having a pore size of approximately 150-300 microns, and a density in the range of 16-21 grams.

In accordance with one preferred aspect of this invention the sponge material making up the cover 122B works better if it is pre-moistened with water. Thus, commercial embodiments of this invention will be preferably packaged wet. Since it is packaged wet, the cover preferably will include an antimicrobial additive to prevent microbial growth. Any suitable commercially available anti-microbial additive can be used, e.g., isothiazolinone treatments, zinc pyrithione, thiabendazole, silver and quaternary ammonium compounds and Polyhexamethylene biguanide (PHMB) and chlorhexidine gluconate (CHG). In addition to helping with storage, the antimicrobial agent inhibits the growth of microbes during use of the system of this invention, reducing the risk of infection.

Operation of the external female catheter 120 is similar to the operation of the external female catheter 20 and is as follows. In particular, the suction regulator 24' operates in an identical manner as the suction regulator 24. Thus, when regulated suction produced by the suction regulator 24' is applied connector 24B' of the port 24B that regulated suction will be applied to the exposed distal portions of the slots 134A-134D and the contiguous open distal ends of the passageways 132A-132D, respectively, to draw any urine that the female patient voided into the cover from there into those passageways, whereupon that urine will be pulled into the interior of the tubing section 124 and carried by air from the suction regulator 24'. From there the urine is carried to the receptacle or canister 12. In particular, with the system 10' as described above when suction is applied from the hospital's suction line or wall regulator 16, that high level of suction is conveyed through the tubing section 14, from whence it is applied to the canister or receptacle 12 and the associated tubing section 18 to the line suction port 24A of the suction regulator 24, whereupon it is regulated (e.g., reduced) by operation of the suction regulator to a much lower operating level, e.g., 40 mmHg. That reduced or regulated suction will appear on the suction port 24B of the regulator 24' and from there to the external catheter 122 to thereby draw urine from the external catheter 122 back through the regulator 24', and out through the tubing section 18 into the receptacle or canister 12 for collection therein.

One of the key features of the integral suction regulator and female catheter 120 allows, like the features of the integral suction regulator and female catheter 20, is that it can be used in a system like 10' to be attached to line suction. This configuration allows for far greater airflow than conventional methods, which aids in urine capture and drying of the catheter. Moreover, the openings through which the regulated suction is applied to the cover 120B is somewhat confined in that only approximately 40 mm of the slots 134A-134D are exposed to provide suction to the contiguous portions of the cover 122B. By decreasing the opening size of the extrusion, i.e., the exposed slots, the subject invention is able to concentrate the same amount of airflow, increasing the velocity of the air to compound the benefits of the high volume of airflow provided by the regulator. However, since the foam component is absorbent regardless of location, over-concentration of the airflow results in location-dependent capture and non-uniform drying and may leave the patient wet or result in leaks. Iterative bench-top testing has suggested providing open slots of approximately 40 mm/1.5 inch results in optimal performance, as defined by the maximum capturable urination rate before the system is overwhelmed and leaks.

As should be appreciated by those skilled in the art, when the tubing in an external catheter circuit becomes filled with urine, either due to a patient urinating a large volume at once, or a temporary occlusion along the circuit, air entrainment is no longer possible, and urine must be pulled through the tubing by the force of suction alone. In this scenario, for any section of tubing traveling along a vertical incline, gravity opposes the suction force limiting the height of any vertical incline which can be overcome. Forty mm of Hg is equivalent to the pressure exerted by approximately 21 inches of water, meaning that for any suction-based urine management system operating at 40 mm Hg no part of the system can have a vertical incline greater than 21 inches without risking failure if the external catheter circuit becomes filled with urine. Conventional external catheter systems, (which may have a tubing path of up to 20 feet between the wall regulator and the patient) present a significant possibility that some portion of the tubing path may have a 21 inch incline, so that such prior art systems are prone to that type of failure if the external catheter circuit becomes filled with urine. In contradistinction, the systems of this invention make use of tubing that is only approximately 6 inches to approximately 24 inches between the regulator and patient's urethra opening. This means that the integrated suction regulators/external catheters of the subject invention should not be prone to failure due to too much urine.

It must be pointed out at this juncture that the various components of the integrated unit 20 and 120 shown and described above are merely exemplary of various components that may be used in accordance with this invention to provide the capabilities as discussed above. Thus, various changes can be made to the integrated external female catheter and suction regulator of subject invention from the exemplary embodiments described above. For example, the use of the optional cover tube 126 can be omitted. In such a case the distal end 124A of the tubing section 124 should extend to approximately 40 mm from the distal end of the end-piece 128, whereupon the tubing section 124 itself closes off the slots in the passageways up to the last (distal) 40 mm of the end-piece. The use of the optional heat shrinkable tube section 126 is a preferred means for covering portions of the slots proximally of the distal-most 40 mm thereof, since heat shrinkable tubing is more economical than the material making up the tubing section 124. Moreover, the end-piece 124, itself, can be constructed so that the slots 134A-134D do not extend the entire length of the associated passageways 132A-132D, but only the distal-most 40 mm thereof. Thus, it is contemplated that the end-piece can be constructed so that only the distal-most portion, e.g., approximately 40 mm, of the passageways 132-132D include slots 134A-134D, so long as the remaining portion of the passageways are configured to carry suction therethrough without leakage and so long as the entire length of the end-piece along which the cover 122B extends is malleable to be conformable to the anatomy of the patient.

Moreover, the suction regulators 24 and 24' may be constructed somewhat similarly to the suction controller 300 shown in FIGS. 9A and 10A of U.S. application Ser. No. 14/227,587 entitled the Gastric Sizing Systems Including Instruments And Methods Of Bariatric Surgery filed on filed on Mar. 27, 2014, now U.S. Pat. No. 10,646,625, which is assigned to the same assignee as this invention and whose disclosure is specifically incorporated by reference herein. That suction controller if used in an integrated unit 20 or 120 like the subject invention would be modified to omit the disk 314 and thus result in a cost saving. In the invention of that patent the disk 314 is provided to seal off the system when positive pressure is applied for leak testing. The integrated unit 20 of this invention and any other integrated units constructed in accordance with this invention will never exceed atmospheric pressure, so a disk 314 is unnecessary. Moreover, the suction controller 300 of that patent if used in an integrated unit like that of this invention will need to be sized and configured to produce the desired regulated suction value, e.g., 40 mmHg.

Various other changes can be made to systems of this invention, in addition to changes in the suction regulator 24 and 24'. For example, some hospitals in which the subject integrated unit will be used have special regulator set-ups that allow for connection of a suction canister directly below the wall regulator. In such a case the tubing section 14 of the system 10 may be omitted. Also, it should be pointed out at this juncture that the integrated units of this invention are not limited to use in hospitals. They can be used in any application providing care to a patient.

Figure 24:
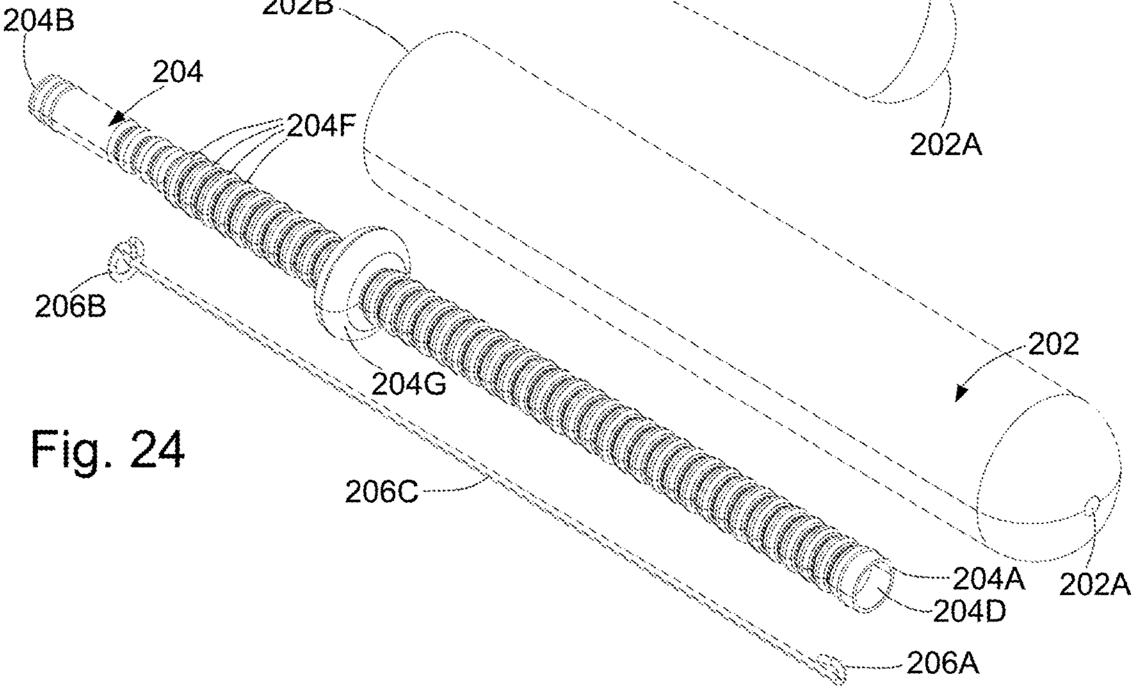
FIG. 24 is an exploded isometric view of the external female catheter of FIG. 22, and showing its three components, namely, a corrugated suction tube, a liquid permeable cover, and a malleable positioning wire.

Moreover, the subject invention is not limited to integrated systems including an external catheter and an integral regulated suction controller. Thus, this invention also contemplates an external female catheter which is a stand-alone device that can be used with any source of regulated suction to remove any urine voided by the female so that the urine can be delivered to some means for collection and disposal. One such exemplary stand-alone external female catheter 200 is shown in FIGS. 22-27. The catheter 200 basically comprises a liquid permeable cover 202, an elongated suction tube 204 and a malleable wire 206 (FIG. 24). The catheter 200 is configured to be position with respect to the female in the same manner as described with respect to the integrated external catheters described above, e.g., with the liquid permeable cover disposed between the female's legs and contiguous with the female's urethra opening.

Figure 26:
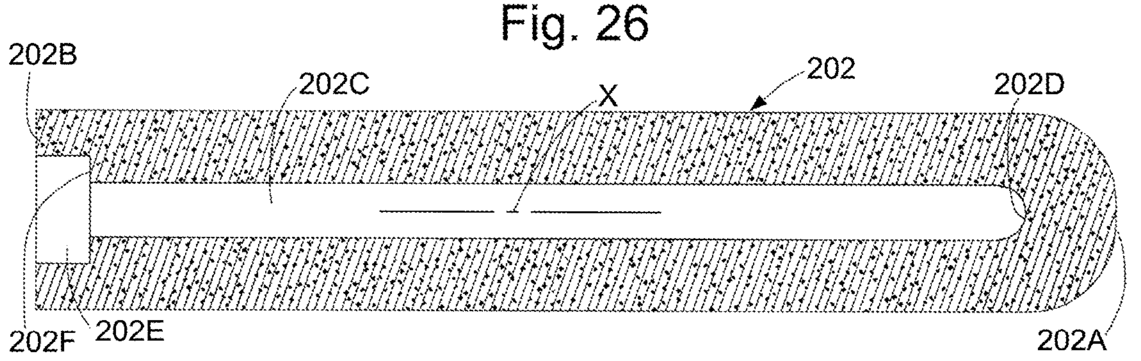
FIG. 26 is a longitudinal sectional view of the liquid permeable cover of FIG. 24.

The cover 202 is a self-supporting cylindrical member formed of a liquid permeable material, preferably one that is absorbent and hydrophilic, e.g., a polyurethane or a PVA (polyvinyl alcohol) sponge. However, it could be formed of other liquid permeable materials such as, cellulose, polyurethane, gauze, etc. As best seen in FIG. 26 the cover 202 is an elongated member cylindrical member having a rounded, e.g., dome-shaped, distal end 202A and a generally planar proximal end 202B. The cover includes a bore 202C extending from the proximal end 202B an interior point 202D (FIG. 26) adjacent the distal end 202A. The bore 202C is centered on the central longitudinal axis X of the cover. The internal diameter of the central bore 202C is approximately the same size or slightly smaller than the external diameter of the suction tube 204 so that the suction tube can be located therein, with the cover 202 held thereon by friction (as will be described later).

In one exemplary embodiment of the catheter 202 the cover is approximately 150 mm in length, with an external diameter of approximately 8 mm. The internal diameter of the bore 202C is approximately 8 mm. The entryway to the bore 202C at the proximal end 202B of the cover is the form of an enlarged diameter annular recess 202E. The recess has a bottom wall 202F. The bottom wall 202F serves as a stop surface for engagement by a portion 204G (to be described later) of the suction tube 204 (to establish the depth to which the suction tube is disposed within the bore 202C (as will also be described later).

Figure 25:
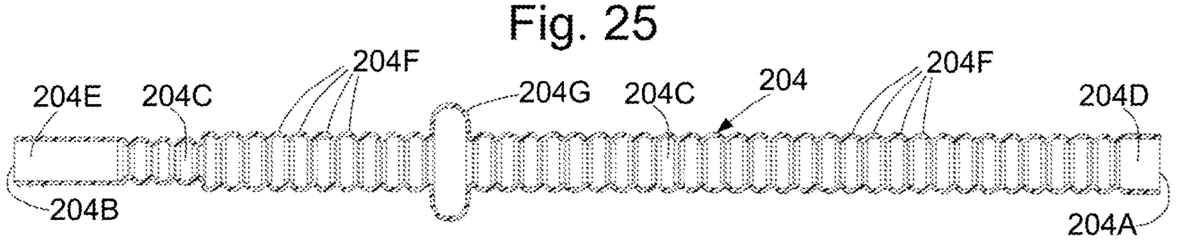
FIG. 25 is a longitudinal sectional view of the corrugated suction tube of FIG. 24.
Figure 27:
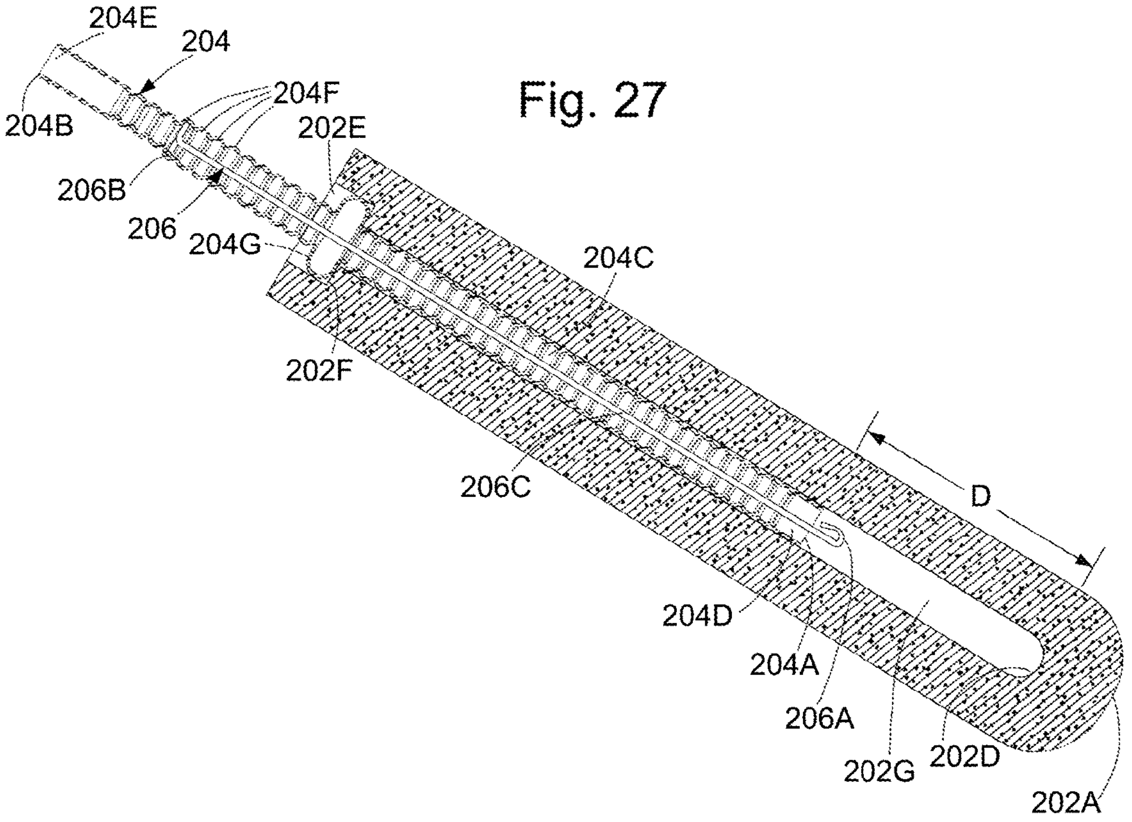
FIG. 27 is a longitudinal sectional view taken along line 27-27 of FIG. 22, wherein a stop portion of the corrugated suction tube abuts a recess in the liquid permeable cover to result in a hollow chamber of a desired length within the liquid permeable cover located distally of the free end of the corrugated suction tube.
Figure 28:
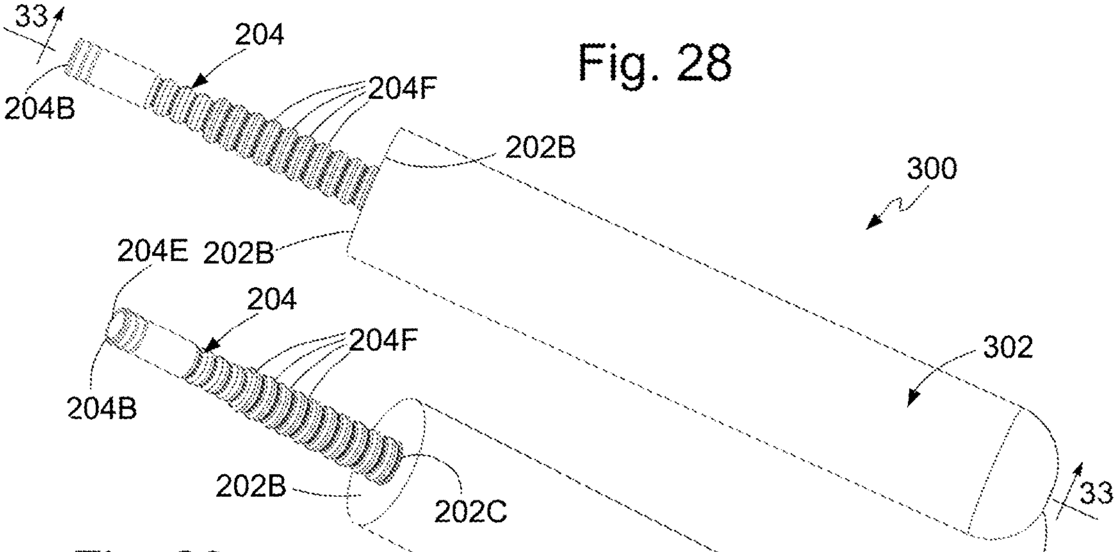
FIG. 28 is a plan view of another exemplary embodiment of an external female catheter constructed in accordance with one aspect of this invention and which external female catheter is also configured to be connected to any source of regulated suction.
Figure 29:
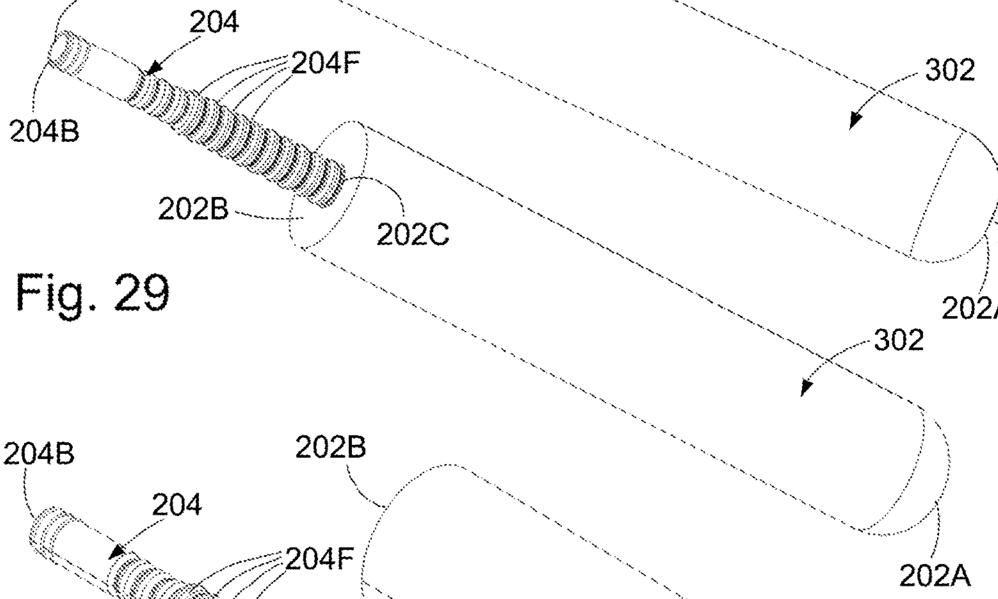
FIG. 29 is an isometric view of the external female catheter of FIG. 28.

The suction tube 204 is best seen in FIGS. 24, 25 and 27 and is an elongated flexible tube having a distal end 204A, a proximal end 202B, with a central passageway 204C extending the length of the tube 204 from the proximal end 204B to the distal end 204A. The suction tube 204 is approximately 190 mm in length. The central passageway 204C is centered on the central longitudinal axis X of the suction tube, and coincident with the central longitudinal axis X of the cover when the cover is mounted on the suction tube. The distal end 204A of the suction tube 204 is open to form a single opening 204D. The proximal end 204B of the suction tube 204 is in the form of a single opening 204E. The sidewall making up the suction tube is unperforated, i.e., it doesn't include any openings or apertures to enable a fluid to pass through the sidewall. The only openings of the suction tube are thus the single opening 204D at the distal end of the suction tube and the single opening 204E at the proximal end of the suction tube. The proximal end of the suction tube is in the form of a conventional fitting or connector to enable the proximal end of the suction tube to be connected to any section of flexible tubing configured for applying regulated suction to the central passageway 202C of the suction tube. That regulated suction can be provided by any suitable suction regulator or other source of suction providing suction at the regulated levels described with respect to the integrated catheter embodiments 20 and 120 described above.

In accordance with one preferred aspect of this invention the sidewall of the suction tube is corrugated, i.e., its sidewall includes sequentially disposed corrugated sections 204F. The sidewall is of a constant wall thickness, e.g., approximately 0.75 mm thick. One of the corrugated sections, namely section 204G, is of an enlarged cross-sectional area, e.g., 16 mm external diameter and is located somewhat adjacent the midpoint of the length of the suction tube, e.g., it is located approximately 75 mm from the proximal end 204B. The enlarged diameter corrugated section 204G serves as a positioning member to establish the depth at which the distal end 204A of suction tube extends into the bore 202C of the cover 202. To that end, the corrugated section 204G has an external diameter which is just slightly less than the internal diameter of the annular recess 202E at the proximal end of the cover so that the corrugated section 204G can be received within that recess to engage the stop surface 202F. That action establishes the depth at which the suction tube 204 extends into the bore 202C of the cover 202. As such, the single opening 204D at the distal end of the suction tube will be located a predetermined distance D, e.g., 30 mm, from the interior point 202D of the cover to result in the creation of an interior chamber 202G having a length D within the cover contiguous with the opening 204D. The chamber 202G is in fluid communication with the passageway 204C of the suction tube via the opening 204D. It should be noted at this juncture that the length of the internal chamber 206D need not be the exemplary length specified above, but can be longer or shorter depending upon the size the external catheter for the particular female.

Accordingly, when the regulated suction is applied at opening 204E at the proximal end of the suction tube 204, that regulated suction will be applied via the single opening 204D to the chamber 202G to draw any urine that the female voided into the cover 202 from there into the chamber 202G. From the chamber 202G the urine will be drawn into the central passageway 204C, whereupon that urine will be carried by air through that passageway and out of the opening 204E for collection by any suitable means (not shown). Such means may be a receptacle or canister 12 like that described earlier or any other collection device that is coupled to the section of flexible tubing (not shown) which is connected to the luer fitting or connector at the proximal end 204B of the suction tube204.

By way of example, but not limitation, the external catheter 200 may be used in a system wherein suction is applied from a hospital's suction line or wall regulator to any conventional suction regulator, like any of various suction regulators sold by Boehringer Laboratories, Inc., the assignee of the subject invention, to reduce the high level of suction to a lower operating level, e.g., 125 mmHg. That reduced or regulated suction will be applied to a canister or some other collection device that is interposed between the flexible tubing section connected to proximal end of the suction tube 204 and the suction regulator. Accordingly, urine withdrawn by the catheter 200 will be collected in the receptacle or canister and will not reach the suction regulator.

The external catheter 200, like the catheters 20 and 120 is configured so that the portion of it which is located between the legs of the female and adjacent her urethra opening is constructed so that it can be bent into a somewhat arcuate shape and retain that shape, whereupon the cover 202 conforms closely and comfortably to the anatomy of the female contiguous with her urethra opening. That feature of catheter 200 is provided by the heretofore identified malleable wire 206.

As best seen in FIG. 24, the malleable wire 206 is an elongated member, formed of any suitable malleable material, e.g., stainless steel, and has a distal end portion 206A, a proximal end portion 206B and an elongated linear intermediate section 206C extending between the proximal end portion and the distal end portion. The proximal end portion 206B is in the form of a circular loop which lies in a plane perpendicular to the longitudinal axis X of the intermediate section. The distal end portion 206A is in the form of a generally J-shape. The length of the malleable wire from its proximal end to its distal end is approximately 150 mm. The outside diameter of the loop 206B is slightly less than the internal diameter of the corrugated sections 204F of the suction tube so that it can be located within one of those corrugated sections whereupon the generally J-shape distal end 206A of the wire 206 is located adjacent the distal end 204A of the suction tube like shown in FIG. 27. Accordingly, the intermediate section 206C of the malleable wire 206 will extend a substantial length of the cover 202, so that the portion of the catheter's cover 202 through which the malleable wire 206 extends can be bent into an arc to conform to the anatomy of the female.

Turning now to FIGS. 28-33 there is shown another alternative embodiment 300 of a stand-alone external female catheter that can be used with any source of regulated suction to remove any urine voided by the female so that the urine can be delivered to some means for collection and disposal. The catheter 300 basically comprises a liquid permeable cover 302, an elongated suction tube 304 and a malleable wire 206. The catheter 300 is configured to be positioned with respect to the female in the same manner as described with respect to the catheter 200.

Figure 32:
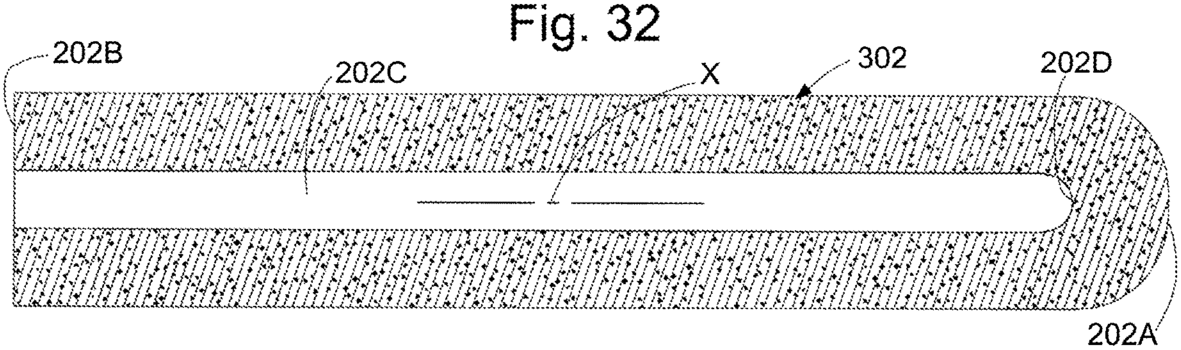
FIG. 32 is a longitudinal sectional view of the liquid permeable cover of FIG. 30.

The cover 302 is a self-supporting cylindrical member formed of a liquid permeable material like that the cover 202. In fact, the cover 302 is identical to the cover 202 except for the construction of its central bore 302C. In the interest of brevity, the common features of the cover 302 with respect to the cover 202 will be given the same reference numbers and the details of their construction, arrangement, and operation will not be reiterated in the interest of brevity. Thus, as can be seen in FIG. 32 the proximal end of the central bore 302 does not include an enlarged diameter annular recess 202E, like the cover 202. The reason is that the embodiment of the stand-alone catheter 300 does not make use of a stop surface of the cover and an enlarged diameter corrugated section of the suction to act as positioning members establishing the distance that the suction tube can be extended into the bore 302C of the cover 302. Rather, the malleable wire 206 provides that positioning function in cooperation with the suction tube 304.

Figure 30:
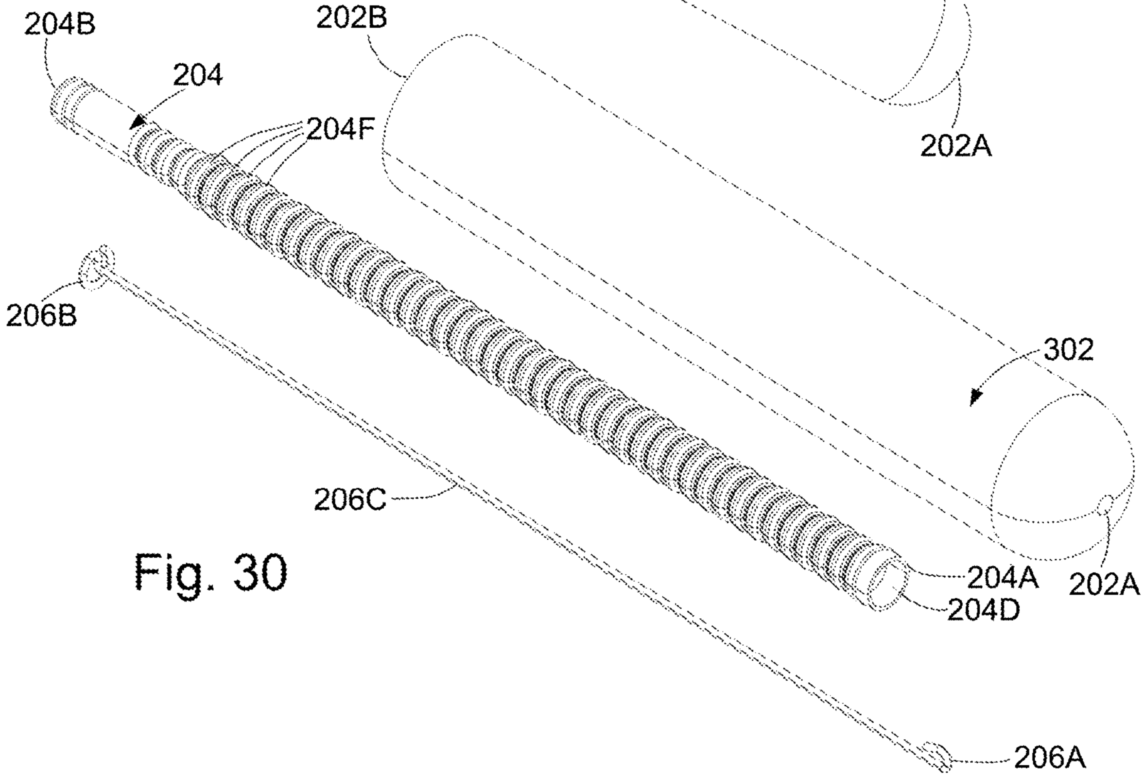
FIG. 30 is an exploded isometric view of the external female catheter of FIG. 28, and showing its three components, namely, a corrugated suction tube, a liquid permeable cover, and a malleable positioning wire.
Figure 31:
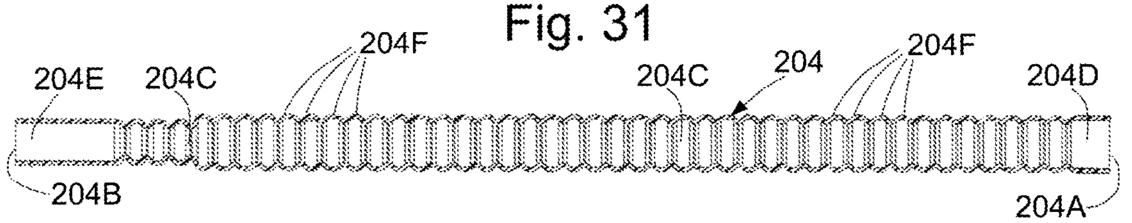
FIG. 31 is a longitudinal sectional view of the corrugated suction tube of FIG. 30.
Figure 33:
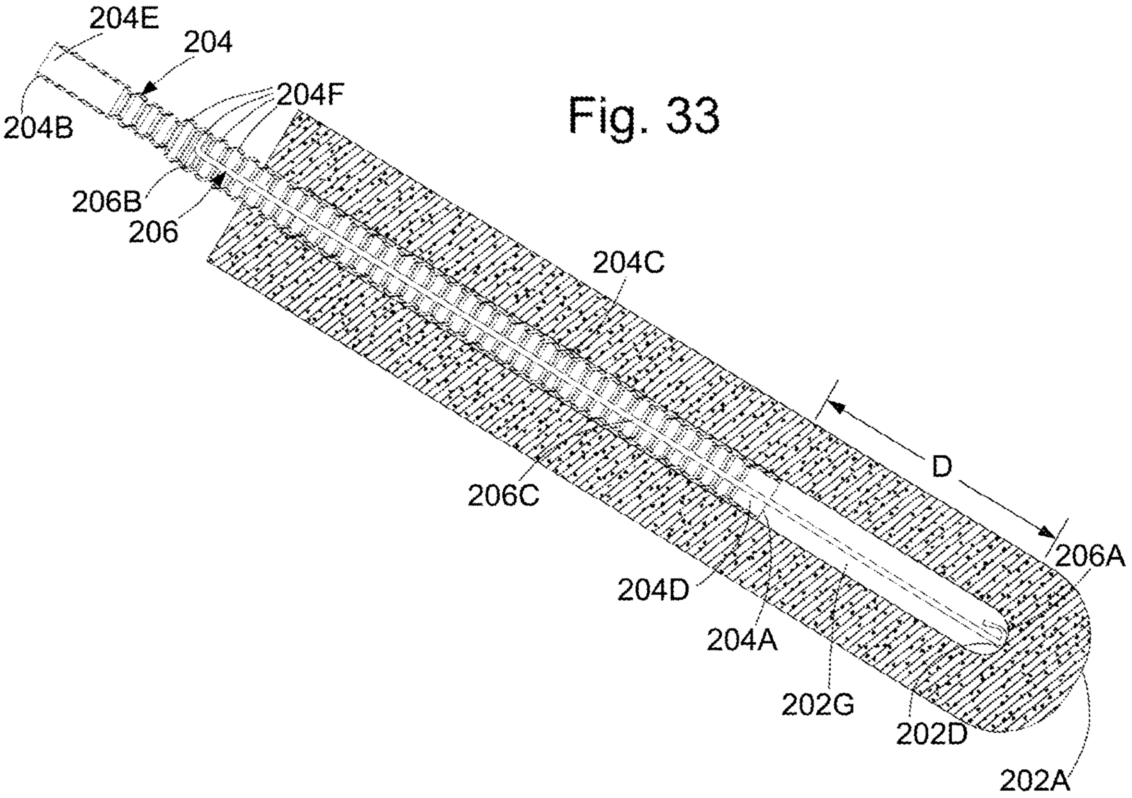
FIG. 33 is a longitudinal sectional view taken along line 33-33 of FIG. 28, wherein the positioning wire is shown positioning the liquid permeable cover with respect to the corrugated suction tube to result in a hollow chamber of a desired length within the liquid permeable cover located distally of the free end of the corrugated suction tube.

As best seen in FIGS. 30, 31 and 33 the suction tube 304 is an elongated flexible tube similar to the flexible suction tube 204. In fact, the suction tube 304 is identical to the suction tube 204 except that it does not include an enlarged cross-section corrugation 204G since it is not necessary to effect the positioning of the cover 302 with respect to the suction tube 304. In the interest of brevity the common features of the suction tube 304 with respect to the suction tube 204 will be given the same reference numbers and the details of their construction, arrangement, function and operation will not be reiterated in the interest of brevity. Thus, as can be seen the suction tube 304 includes a distal end 204A, a proximal end 202B, with a central passageway 204C extending the length of the tube 204 from the proximal end 204B to the distal end 204A. The sidewall of the suction tube between it proximal end and its distal end includes the plural corrugations 204F. The passageway 204C is centered on the central longitudinal axis X of the tube, and coincident with the central longitudinal axis X of the cover 302 when the cover is mounted on the suction tube 304. The distal end 204A of the suction tube 304 is open to form a single opening 204D. The proximal end 204B of the tube 304 is in the form of a single opening 204E. The sidewall making up the suction tube 304 is unapertured so that it doesn't include any openings or apertures, whereupon the only openings of the suction tube 304 are the single opening 204D at the distal end of the suction tube and the single opening 204E at the proximal end of the suction tube. The proximal end of the suction tube is in the form of a conventional fitting or connector to enable the proximal end of the suction tube to be connected to any section of flexible tubing configured for applying regulated suction to the central passageway 304C of the suction tube.

The malleable wire 206 of the catheter 300 is identical in construction to the malleable wire 206 of the catheter 200 except that its intermediate section 206C is of a longer length than the intermediate section of the malleable wire of the catheter 200. The malleable wire 206 of the catheter 300 also serves the same function as the malleable wire 206 of the catheter 200 in that it enables the portion of the cover through which the malleable wire 206 extends can be bent into a somewhat arcuate shape, whereupon the cover 302 conforms closely and comfortably to the anatomy of the patient contiguous with the patient's urethra opening. In addition, as mentioned above, the malleable wire 206 of the catheter 300 also serves as a means for positioning the cover 302 with respect to the suction tube 304. To that end, the loop 206B at the proximal end of the malleable wire 206 is disposed within a selected one of the corrugated sections 304F of the suction tube 304 somewhat close to the proximal end of the suction tube, whereupon the generally J-shape distal end 206A of the wire 206 extends out of the open distal end 304A of the suction tube to engage the distal end of the bore 202D at the intermediate point. As such, the single opening 204D at the distal end of the suction tube 204 will be located a predetermined distance D, e.g., 30 mm, from the interior point 202D of the cover 302. That action results in the creation of an interior chamber 202G having a length D within the cover 302. The chamber 202G is in fluid communication with the passageway 204C of the suction tube via the single opening 204D. Moreover, the intermediate section of the malleable wire 206 extends a substantial length of the cover 302, so that the portion of the catheter's cover 302 through which the malleable wire 206 extends can be bent into an arc to conform to the anatomy of the female.

The stand-alone catheter 300 operates in the same manner as the stand-alone catheter 200. In particular, when the regulated suction is applied at opening 204E of the suction tube 304, that regulated suction will be applied via the single opening 204D to the chamber 202G, to draw any urine that the female patient voided into the cover 302 from there into the chamber 202G and from there into the central passageway 204C, whereupon that urine will be carried by air through that passageway and out of the opening 204E for collection by means (not shown). Such means may be a receptacle or canister 12 like that described earlier or any other collection device that is coupled to the section of flexible tubing (not shown) which is connected to the luer connector at the proximal end 204B of the suction tube204.

It should be pointed out at this juncture that the embodiments of the stand-alone external catheters 200 and 300 are merely exemplary of various stand-alone external catheters that can be constructed in accordance with this invention. Thus, various changes to the stand-alone external catheters of this invention and their components can be made within the scope of this invention. For example, the various dimensions and materials identified heretofore may be changed. Moreover, the suction tube need not be corrugated, so long as it is flexible and provides some means to enable a malleable wire (or some other elongated malleable member) to be coupled to it to facilitate the shaping of the portion of the catheter that will be contiguous with female's urethra opening. Moreover, if desired, a non-corrugated suction tube can be constructed in accordance with this invention to include a positioning member to cooperate with a portion of the cover for establishing the depth to which the suction tube can be extended into the cover to establish an internal chamber of a desired length contiguous with the single opening at the distal end of the suction tube. Other changes are also contemplated.

Without further elaboration the foregoing will so fully illustrate our invention that others may, by applying current or future knowledge, adopt the same for use under various conditions of service.

We claim:

1. An antimicrobial cover for use in an external catheter device for automatically removing by suction urine voided at urethra of a female patient, the external catheter device including an elongated suction tube configured for receipt of suction and having a distal end portion including an opening, said antimicrobial cover being held in a package and comprising a generally cylindrically shaped body having a distal end, a proximal end and a bore extending from said proximal end to a point located adjacent said distal end, said generally cylindrically shaped body having a curved external surface, said curved external surface extends around an entire circumference of the generally cylindrically shaped body, the entirety of said curved external surface being exposed when the external catheter device is used to enable any portion of said curved external surface of said antimicrobial cover to be brought into engagement with a portion of the female patient adjacent the urethra of the female patient, said generally cylindrically shaped body being formed of a sponge material which includes an antimicrobial additive configured to prevent microbial growth, whereupon when the external catheter device is used said antimicrobial agent inhibits the growth of microbes.

2. The antimicrobial cover of claim 1, wherein said antimicrobial additive comprises one or more of isothiazolinone treatments, zinc pyrithione, thiabendazole, silver and quaternary ammonium compounds and Polyhexamethylene biguanide (PHMB) and chlorhexidine gluconate (CHG).

3. The antimicrobial cover of claim 2, wherein said sponge material is pre-moistened with water whereupon said antimicrobial cover is initially held in a moist condition within said package.

4. The antimicrobial cover of claim 1, wherein said sponge material is pre-moistened with water whereupon said antimicrobial cover is initially held in a moist condition within said package.

5. A method of preventing or reducing microbial growth on an external catheter device automatically removing by suction urine voided by a patient, the external catheter device including an elongated suction tube configured for receipt of suction and having a distal end portion including an opening, said method comprising:

providing antimicrobial cover comprising a generally cylindrically shaped body having a distal end, a proximal end and a bore extending from said proximal end to a point located adjacent said distal end, said generally cylindrically shaped body having a curved external surface, said curved external surface extends around an entire circumference of the generally cylindrically shaped body, the entirety of said curved external surface being exposed to enable any portion of said curved external surface to be brought into engagement with a portion of the female patient adjacent the urethra of the female patient, said generally cylindrical shaped body being formed of a sponge material and including an antimicrobial additive configured to prevent microbial growth;

providing said antimicrobial cover in a package to keep said antimicrobial cover therein until ready for use;

removing said antimicrobial cover from said package; and applying said antimicrobial cover to bring any portion of said curved external surface into engagement with a portion of the anatomy of the patient adjacent the urethra of the patient, whereupon said antimicrobial agent inhibits the growth of microbes.

6. The method of claim 5, wherein said antimicrobial additive comprises one or more of isothiazolinone treatments, zinc pyrithione, thiabendazole, silver and quaternary ammonium compounds and Polyhexamethylene biguanide (PHMB) and chlorhexidine gluconate (CHG).

7. The method of claim 6, wherein said sponge material is pre-moistened with water whereupon said antimicrobial cover is initially held in a moist condition within said package.

8. The method of claim 5, wherein said sponge material is pre-moistened with water whereupon said antimicrobial cover is initially held in a moist condition within said package.

* * * * *